(12) United States Patent
Mantlo et al.

(10) Patent No.: US 7,504,433 B2
(45) Date of Patent: Mar. 17, 2009

(54) THIOPHENE DERIVATIVE PPAR MODULATORS

(75) Inventors: Nathan Bryan Mantlo, Brownsburg, IN (US); Xiaodong Wang, Carmel, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 222 days.

(21) Appl. No.: 10/540,330

(22) PCT Filed: Dec. 31, 2003

(86) PCT No.: PCT/US03/39118

§ 371 (c)(1), (2), (4) Date: Jun. 21, 2005

(87) PCT Pub. No.: WO2004/063184

PCT Pub. Date: Jul. 29, 2004

(65) Prior Publication Data

US 2006/0094768 A1     May 4, 2006

Related U.S. Application Data

(60) Provisional application No. 60/438,587, filed on Jan. 6, 2003.

(51) Int. Cl.
*A61K 31/381*     (2006.01)
*C07D 333/16*     (2006.01)

(52) U.S. Cl. .................... 514/438; 549/78
(58) Field of Classification Search .............. 549/62, 549/70, 71, 78; 514/445, 438
See application file for complete search history.

(56) References Cited

U.S. PATENT DOCUMENTS 7,091,237 B2 *   8/2006   Beswick et al. ............. 514/438

FOREIGN PATENT DOCUMENTS

WO     WO 02/28821 A     4/2002
WO     WO 02/092590 A    11/2002

OTHER PUBLICATIONS

Bailey et al. Nature Immunology 2005, 6(10), 966-967.*
Morissette et al. Advanced Drug Delivery Reviews 2004, 56, 275-300.*

* cited by examiner

*Primary Examiner*—Kamal A Saeed
*Assistant Examiner*—Jason Nolan
(74) *Attorney, Agent, or Firm*—MaCharri Vorndran-Jones

(57) ABSTRACT

The present invention is directed to compounds represented by the following structural formula, Formula I: and stereoisomers, pharmaceutically acceptable salts, solvates and hydrates thereof, wherein: (a) X is selected from the group consisting of O, S, S(O)2, N, and a bond; (b) U is an aliphatic linker wherein one carbon atom of the aliphatic linker may be replaced with O, NH or S, and wherein such aliphatic linker is optionally substituted with R30; (c) Y is selected from the group consisting of C, O, S, NH and a single bond; and (d) E is C(R3)(R4)A or A.

36 Claims, No Drawings

THIOPHENE DERIVATIVE PPAR MODULATORS

This application is a United States national phase entry, pursuant to 35 U.S.C. 371, of PCT/US2003/039118, filed on Dec. 31, 2003, hereby incorporated by reference in it's entirety, which claims the benefit of United States provisional patent application Ser. No. 60/438587, filed Jan. 6, 2003 incorporated herein by reference.

BACKGROUND OF THE INVENTION

Peroxisome Proliferator Activated Receptors (PPARs) are members of the nuclear hormone receptor superfamily, a large and diverse group of proteins that mediate ligand-dependent transcriptional activation and repression. Three subtypes of PPARs have been isolated: PPARα, PPARγ and PPARδ.

The expression profile of each isoform differs significantly from the others, whereby PPARα is expressed primarily, but not exclusively in liver; PPARγ is expressed primarily in adipose tissue; and PPARδ is expressed ubiquitously. Studies of the individual PPAR isoforms and ligands have revealed their regulation of processes involved in insulin resistance and diabetes, as well as lipid disorders, such as hyperlipidemia and dyslipidemia. PPARγ agonists, such as pioglitazone, can be useful in the treatment of non-insulin dependent diabetes mellitus. Such PPARγ agonists are associated with insulin sensitization.

PPARα agonists, such as fenofibrate, can be useful in the treatment of hyperlipidemia. Although clinical evidence is not available to reveal the utility of PPARδ agonists in humans, several preclinical studies suggest that PPARδ agonists can be useful in the treatment of diabetes and lipid disorders.

The prevalence of the conditions that comprise Metabolic Syndrome (obesity, insulin resistance, hyperlipidemia, hypertension and atherosclerosis) continues to increase. New pharmaceutical agents are needed to address the unmet clinical needs of patients.

PPARδ agonists have been suggested as a potential treatment for use in regulating many of the parameters associated with Metabolic Syndrome and Atherosclerosis. For example, in obese, non-diabetic rhesus monkeys, a PPARδ agonist reduced circulating triglycerides and LDL, decreased basal insulin levels and increased HDL (Oliver, W. R. et al. Proc Natl Acad Sci 98:5306-5311; 2001). The insulin sensitization observed with the use of a PPARδ agonist is thought to be in part due to decreased myocellular lipids (Dressel, U. et al. Mol Endocrinol 17:2477-2493; 2003).

Further, atherosclerosis is considered to be a disease consequence of dyslipidemia and may be associated with inflammatory disease. C-reactive protein (CRP) production is part of the acute-phase response to most forms of inflammation, infection and tissue damage. It is measured diagnostically as a marker of low-grade inflammation. Plasma CRP levels of greater than 3 mg/L have been considered predictive of high risk for coronary artery disease (J. Clin. Invest 111: 1085-1812, 2003).

PPARδ agonists are believed to mediate anti-inflammatory effects. Indeed, treatment of LPS-stimulated macrophages with a PPARδ agonist has been observed to reduce the expression of iNOS, IL12, and IL-6 (Welch, J. S. et al. Proc Natl Acad Sci 100:6712-67172003).

It may be especially desirable when the active pharmaceutical agent selectively modulates a PPAR receptor subtype to provide an especially desirable pharmacological profile. In some instances, it can be desirable when the active pharmacological agent selectively modulates more than one PPAR receptor subtype to provide a desired pharmacological profile.

SUMMARY OF THE INVENTION

The present invention is directed to compounds represented by the following structural Formula I':

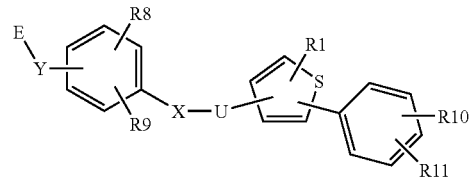

and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, phenyl, aryl-$C_{1-4}$-heteroalkyl, heteroaryl, and C3-C6 cycloalkylaryl-$C_{0-2}$-alkyl, and wherein $C_1$-$C_8$ alkyl is optionally substituted with from one to three substituents independently selected from R1'; and further wherein $C_1$-$C_8$ alkenyl, phenyl, aryl-$C_{1-4}$-heteroalkyl, heteroaryl, and C3-C6 cycloalkylaryl-$C_{0-2}$-alkyl, are each optionally substituted with from one to three substituents independently selected from R2;

(b) R1' are each independently selected from the group consisting of hydroxy, cyano, nitro, halo, oxo, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{1-4}$-alkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17; R18, R19, R20, R21, R22, R23, R24 and R25 are each independently selected from the group consisting of hydrogen, $C_1$-$C_6$ alkyl and aryl;

(c) R2, R26, R27, R28, and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$;

(d) X is selected from the group consisting of O, S, S(O)$_2$, N and a bond;

(e) U is an aliphatic linker wherein one carbon atom of the aliphatic linker is optionally replaced with O, NH or S, and wherein such aliphatic linker is optionally substituted with from one to four substituents each independently selected from R30;

(f) Y is selected from the group consisting of C, NH, and a single bond;

(g) E is C(R3)(R4)A or A and wherein (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1$-$C_6$ haloalkyl, aryl $C_0$-$C_4$ alkyl and $C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

with the proviso that when R1 is $C_1$-$C_8$ alkyl, Y is in a para-substituted position with relation to X, and X is selected from the group consisting of a bond and O, then R4 is selected from the group consisting of $C_1$-$C_5$ alkoxy, aryloxy, and aryl$C_0$-$C_4$ alkyl; with the additional proviso that when R1 is $C_1$-$C_8$ alkyl, Y is in a para substituted position with relation to X, X is S, and U is optionally substituted methylene, then R4 is selected from the group consisting of $C_1$-$C_5$ alkoxy, aryloxy, and aryl$C_0$-$C_4$ alkyl;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(j) R10, R11 are each independently selected from the group consisting of hydrogen, hydroxy, cyano, nitro, halo, oxo, $C_1$-$C_6$ alkyl, $C_1$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28;

(k) R12', R12", R13', R14', R15', R16', R17', R18', R19', R20', R21', R22', R23', R24', and R25' are each independently selected from the group consisting of hydrogen, $C_1$-$C_6$ alkyl and aryl; and (l) R30 is selected from the group consisting of $C_1$-$C_6$ alkyl, aryl-$C_{0-4}$-alkyl, aryl, $C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31. A further embodiment of the present invention is a compound of the Formula I":

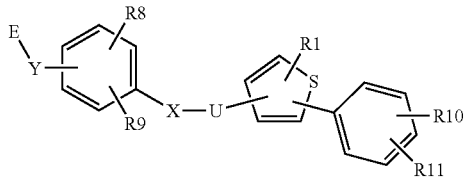

and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, phenyl, aryl-$C_{1-4}$-heteroalkyl, heteroaryl, and C3-C6 cycloalkylaryl-$C_{0-2}$-alkyl, and wherein $C_1$-$C_8$ alkyl is optionally substituted with from one to three substituents independently selected from R1'; and further wherein $C_1$-$C_8$ alkenyl, phenyl, aryl-$C_{1-4}$-heteroalkyl, heteroaryl, and C3-C6 cycloalkylaryl-$C_{0-2}$-alkyl, are each optionally substituted with from one to three substituents independently selected from R2;

(b) R1' are each independently selected from the group consisting of hydroxy, cyano, nitro, halo, oxo, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{1-4}$-alkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2, R26, R27, R28, and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$;

(d) X is selected from the group consisting of O, S, S(O)$_2$, N and a bond;

(e) U is an aliphatic linker wherein one carbon atom of the aliphatic linker is optionally replaced with O, NH or S, and wherein such aliphatic linker is substituted with from one to four substituents each independently selected from R30;

(f) Y is selected from the group consisting of C, O, S, NH and a single bond;

(g) E is C(R3)(R4)A or A and wherein (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1$-$C_6$haloalkyl, aryl $C_0$-$C_4$ alkyl and $C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

with the proviso that when R1 is $C_1$-$C_8$ alkyl, Y is in a para substituted position with relation to X, and X is selected from the group consisting of a bond and O, then R4 is selected from the group consisting of $C_1$-$C_5$ alkoxy, aryloxy, and aryl$C_0$-$C_4$ alkyl; with the additional proviso that when R1 is $C_1$-$C_8$ alkyl, Y is in a para substituted position with relation to X, X is S, and U is optionally substituted methylene, then R4 is selected from the group consisting of $C_1$-$C_5$ alkoxy, aryloxy, and aryl$C_0$-$C_4$ alkyl;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(j) R10, R11 are each independently selected from the group consisting of hydrogen, hydroxy, cyano, nitro, halo, oxo, $C_1$-$C_6$ alkyl, $C_1$-$C_6$ alkyl-COOR12'', $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28;

(k) R12', R12'', R13', R14', R15', R16', R17', R18', R19', R20', R21', R22', R23', R24', and R25' are each independently selected from the group consisting of hydrogen, $C_1$-$C_6$ alkyl and aryl; and (l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31. Yet another embodiment of the present invention is a compound of the Formula I''':

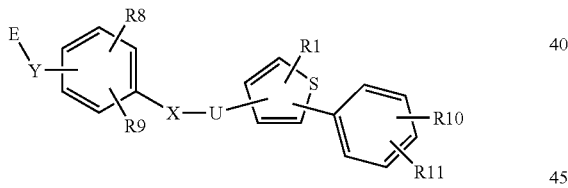

and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, phenyl, aryl-$C_{1-4}$-heteroalkyl, heteroaryl, and C3-C6 cycloalkylaryl-$C_{0-2}$-alkyl, and wherein $C_1$-$C_8$ alkyl is optionally substituted with from one to three substituents independently selected from R1'; and further wherein $C_1$-$C_8$ alkenyl, phenyl, aryl-$C_{1-4}$-heteroalkyl, heteroaryl, and C3-C6 cycloalkylaryl-$C_{0-2}$-alkyl, are each optionally substituted with from one to three substituents independently selected from R2;

(b) R1' are each independently selected from the group consisting of hydroxy, cyano, nitro, halo, oxo, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{1-4}$-alkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2, R26, R27, R28, and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16', N(R17)$_2$, NR18C(O)R19, NR20SO$_2$R21, SR22, S(O)R23, S(O)$_2$R24, and S(O)$_2$N(R25)$_2$;

(d) X is selected from the group consisting of O, S, S(O)$_2$, N and a bond;

(e) U is an aliphatic linker wherein one carbon atom of the aliphatic linker is optionally replaced with O, NH or S, and wherein such aliphatic linker is optionally substituted with from one to four substituents each independently selected from R30;

(f) Y is selected from the group consisting of C, O, S, NH and a single bond;

(g) E is C(R3)(R4)A or A and wherein (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1$-$C_6$ haloalkyl, aryl $C_0$-$C_4$ alkyl and $C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

with the proviso that when R1 is $C_1$-$C_8$ alkyl, Y is in a para substituted position with relation to X, and X is selected from the group consisting of a bond and O, then R4 is selected from the group consisting of $C_1$-$C_5$ alkoxy, aryloxy, and aryl$C_0$-$C_4$ alkyl; with the additional proviso that when R1 is $C_1$-$C_8$ alkyl, Y is in a para substituted position with relation to X, X is S, and U is optionally substituted methylene, then R4 is selected from the group consisting of $C_1$-$C_5$ alkoxy, aryloxy, and aryl$C_0$-$C_4$ alkyl;

with the further proviso that when Y is O then R4 is selected from the group consisting of $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(j) R10, R11 are each independently selected from the group consisting of hydrogen, hydroxy, cyano, nitro, halo, oxo, $C_1$-$C_6$ alkyl, $C_1$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28;

(k) R12', R12", R13', R14', R15', R16', R17', R18', R19', R20', R21', R22', R23', R24', and R25' are each independently selected from the group consisting of hydrogen, $C_1$-$C_6$ alkyl and aryl; and (l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31.

An embodiment of the present invention is a compound of the structural Formula I:

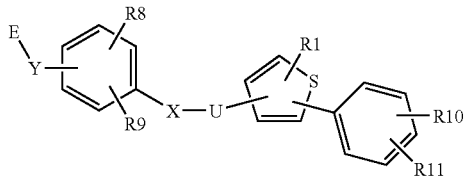

and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, phenyl, aryl-$C_{1-4}$-heteroalkyl, heteroaryl, and C3-C6 cycloalkylaryl-$C_{0-2}$-alkyl, and wherein $C_1$-$C_8$ alkyl is optionally substituted with from one to three substituents independently selected from R1'; and further wherein $C_1$-$C_8$ alkenyl, phenyl, aryl-$C_{1-4}$-heteroalkyl, heteroaryl, and C3-C6 cycloalkylaryl-$C_{0-2}$-alkyl, are each optionally substituted with from one to three substituents independently selected from R2;

(b) R1' are each independently selected from the group consisting of hydroxy, cyano, nitro, halo, oxo, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{1-4}$-alkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2, R26, R27, R28, and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$-cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$;

(d) X is selected from the group consisting of O, S, S(O)$_2$, N and a bond;

(e) U is an aliphatic linker wherein one carbon atom of the aliphatic linker may be replaced with O, NH or S, and wherein such aliphatic linker is optionally substituted with R30;

(f) Y is selected from the group consisting of C, O, S, NH and a single bond;

(g) E is C(R3)(R4)A or A and wherein
 (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from $R^7$;
 (ii) each $R^7$ is independently selected from the group consisting of hydrogen, $C_1$-$C_6$ haloalkyl, aryl $C_0$-$C_4$ alkyl and $C_1$-$C_6$ alkyl;
 (iii) R3 is selected from the group consisting of hydrogen, $C_1$-$C_5$ alkyl, and $C_1$-$C_5$ alkoxy; and
 (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26;
 with the proviso that when R1 is $C_1$-$C_8$ alkyl, Y is in a para substituted position with relation to X, and X is selected from the group consisting of a bond and O, then R4 is selected from the group consisting of $C_1$-$C_5$ alkoxy, aryloxy, and aryl$C_0$-$C_4$ alkyl; with the additional proviso that when R1 is $C_1$-$C_8$ alkyl, Y is in a para substituted position with relation to X, X is S, and U is optionally substituted methylene, then R4 is selected from the group consisting of $C_1$-$C_5$ alkoxy, aryloxy, and aryl$C_0$-$C_4$ alkyl;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ allyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;

(j) R10, R11 are each independently selected from the group consisting of hydrogen, hydroxy, cyano, nitro, halo, oxo, $C_1$-$C_6$ alkyl, $C_1$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28;

(k) R12', R12", R13', R14', R15', R16', R17', R18', R19', R20', R21', R22', R23', R24', and R25' are each independently selected from the group consisting of hydrogen, $C_1$-$C_6$ alkyl and aryl; and (l) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31.

In one embodiment, the present invention also relates to pharmaceutical compositions comprising at least one compound of the present invention, or a pharmaceutically acceptable salt, solvate, hydrate, or stereoisomer thereof, and a pharmaceutically acceptable carrier.

In another embodiment, the present invention relates to a method of selectively modulating a PPAR delta receptor by contacting the receptor with at least one compound represented by Structural Formula I, or a pharmaceutically acceptable salt, solvate, hydrate, or stereoisomer thereof.

In another embodiment, the present invention relates to a method of modulating one or more of the PPAR alpha, beta, gamma, and/or delta receptors.

In a further embodiment, the present invention relates to a method of making a compound represented by Structural Formula I.

The compounds of the present invention are believed to be effective in treating and preventing Metabolic syndrome, Type II diabetes, hyperglycemia, hyperlipidemia, obesity, coagaulopathy, hypertension, atherosclerosis, and other disorders related to Metabolic syndrome and cardiovascular diseases. Further, compounds of this invention can be useful for lowering fibrinogen, increasing HDL levels, treating renal disease, controlling desirable weight, treating demyelinating diseases, treating certain viral infections, and treating liver disease. In addition, the compounds can be associated with fewer clinical side effects than compounds currently used to treat such conditions.

DETAILED DESCRIPTION OF THE INVENTION

The terms used to describe the instant invention have the following meanings.

As used herein, the term "aliphatic linker" or "aliphatic group" is a non-aromatic, consisting solely of carbon and hydrogen and may optionally contain one or more units of unsaturation, e.g., double and/or triple bonds (also refer herein as "alkenyl" and "alkynyl"). An aliphatic or aliphatic group may be straight chained, branched (also refer herein as "alkyl") or cyclic (also refer herein as "cycloalkyl). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e. completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like. It can be a preferred embodiment of the present invention that one carbon atom of the aliphatic linker is replaced with an O, NH, or S. It may further be preferred that the aliphatic linker is substituted with from one to four substituents each independently selected from R30. It may be preferred that the aliphatic linker is substituted with two substituents each independently selected from R30.

The term "alkyl," unless otherwise indicated, refers to those alkyl groups of a designated number of carbon atoms of either a straight or branched saturated configuration. As used herein, "$C_0$ alkyl" means that there is no carbon and therefore represents a bond. Examples of "alkyl" include, but are not limited to, methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above. As used herein, the term "alkyloxo" means an alkyl group of the designated number of carbon atoms with a "=O" substituent.

The term "alkenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "alkynyl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with designated number of substituents as set forth in the embodiment recited above.

The term "heteroalkyl" refers to a means hydrocarbon chain of a specified number of carbon atoms wherein at least one carbon is replaced by a heteroatom selected from the group consisting of O, N and S.

The term "cycloalkyl" refers to a saturated or partially saturated carbocycle containing one or more rings of from 3 to 12 carbon atoms, typically 3 to 7 carbon atoms. Examples of cycloalkyl includes, but are not limited to cyclopropyl, cyclobutyl, cyclopentyl, cyclohexyl and cycloheptyl, and the like. "Cycloalkyaryl" means that an aryl is fused with a cycloalkyl, and "Cycloalkylaryl-alkyl" means that the cycloalkylaryl is linked to the parent molecule through the alkyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. An example of a haloalkyl group is trifluoromethyl ($CF_3$); however, the term is in no way limited to trifluoromethyl. Trihalomethyl can be a preferred haloalkyl group.

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "aryl" includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3, 4-tetrahydronaphthyl). "Aryl" as defined above may be optionally substituted with a designated number of substituents as set forth in the embodiment recited above. A preferred aryloxy group can be phenoxy, wherein the O is linked to the parent molecule.

The term "arylalkyl" refers to an aryl alkyl group which is linked to the parent molecule through the alkyl group, which may be further optionally substituted with a designated number of substituents as set forth in the embodiment recited above. One preferred arylalkyl group can be benzyl or phenyl. When arylalkyl is aryl$C_0$alkyl, then the aryl group is bonded directly to the parent molecule. Likewise, arylheteroalkyl means an aryl group linked to the parent molecule through the heteroalkyl group.

The term "acyl" refers to alkylcarbonyl species.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from the group consisting of O, N, and S. The "heteroaryl" as defined above may be optionally substituted with a designated number of substituents as set forth in the embodiment recited above. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like. The term "heteroarylalkyl" means that the heteroaryl group is linked to the parent molecule through the alkyl portion of the heteroarylalkyl.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N or S. The "heterocycloalkyl" as defined above may be optionally substituted with a designated number of substituents as set forth in the embodiment recited above. Examples of heterocycloalkyl include, but are not limited to, morpholine, piperidine, piperazine, pyrrolidine, and thiomorpholine. As used herein, alkyl groups include straight chained and branched hydrocarbons, which are completely saturated.

As used herein, the phrase "selectively modulate" means a compound whose EC50 for the stated PPAR receptor is at least ten fold lower than its EC50 for the other PPAR receptor subtypes.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated using methods familiar to the skilled artisan. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

"Pharmaceutically-acceptable salt" refers to salts of the compounds of the Structural Formula I which are considered to be acceptable for clinical and/or veterinary use. Typical pharmaceutically-acceptable salts include those salts prepared by reaction of the compounds of the present invention with a mineral or organic acid or an organic or inorganic base. Such salts are known as acid additiona salts and base addition salts, respectively. It will be recognized that the particular counterion forming a part of any salt of this invention is not of a critical nature, so long as the salt as a whole is pharmaceutically-acceptable and as long as the counterion does not contribute undesired qualities to the salt as a whole. These salts may be prepared by methods known to the skilled artisan.

The compounds of Structural Formula I may contain one or more chiral centers, and exist in different optically active forms. When compounds of Structural Formula I contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of Structural Formula I may exist in different stable conformational forms that may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

Certain compounds of Structural Formula I and their salts may also exist in the form of solvates, for example hydrates, and the present invention includes each solvate and mixtures thereof.

The term, "active ingredient" means the compounds generically described by Structural Formula I as well as the sterioisomers, salts, solvates, and hydrates, The term "pharmaceutically acceptable" means that the carrier, diluent, excipients and salt are pharmaceutically compatible with the other ingredients of the composition. Pharmaceutical compositions of the present invention are prepared by procedures known in the art using well known and readily available ingredients.

"Preventing" refers to reducing the likelihood that the recipient will incur or develop any of the pathological conditions described herein. The term "preventing" is particularly applicable to a patient that is susceptible to the particular patholical condition.

"Treating" refers to mediating a disease or condition and preventing, or mitigating, its further progression or ameliorate the symptoms associated with the disease or condition.

"Pharmaceutically-effective amount" means that amount of active ingredientit, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a selected PPAR receptor or to prevent or mediate a disease or condition. Generally, the effective amount of a Compound of Formula I will be between 0.02 through 5000 mg per day. Preferably the effective amount is between 1 through 1,500 mg per day. Preferably the dosage is from 1 through 1,000 mg per day.

The desired dose may be presented in a single dose or as divisded doses administered at appropriate intervals.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like. The physician of ordinary skill will know how to identify humans who will benefit from administration of the compounds and compositions of the present invention.

The present invention further provides a method for the treatment and/or prophylaxis of hyperglycemia in a human or non-human mammal which comprises administering an effective amount of active ingredient, as defined herein, to a hyperglycemic human or non-human mammal in need thereof.

The invention also relates to the use of a compound of Formula I as described above, for the manufacture of a medicament for treating a PPAR receptor mediated condition.

A therapeutically effective amount of a compound of Structural Formula I can be used for the preparation of a medicament useful for treating Metabolic syndrome, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

When used herein Metabolic syndrome includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I, a stereoisomer, salt, solvate and/or hydrate thereof ("Active Igredient") and one or more additional active agents, as well as administration of a compound of Active Ingredient and each active agent in its own separate pharmaceutical dosage formulation. For example, an Active Ingredient and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, an Active Ingredient and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein an Active Ingredient is administered in combination with one or more of the following active agents: antihyperlipidemic agents; plasma HDL-raising agents; antihypercholesterolemic agents, fibrates, vitamins, aspirin, and the like. As noted above, the Active Ingredient can be administered in combination with more than one additional active agent.

Another example of combination therapy can be seen in treating diabetes and related disorders wherein the Active Ingredient can be effectively used in combination with, for example, sulfonylureas, biguanides, thiazolidinediones, α-glucosidase inhibitors, other insulin secretogogues, insulin as well as the active agents discussed above for treating atherosclerosis.

The Active Ingredients of the present invention, have valuable pharmacological properties and can be used in pharmaceutical compositions containing a therapeutically effective amount of Active Ingredient of the present invention, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the Active Ingredient of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the Active Ingredient of the present invention, calculated to produce the desired therapeutic effect, in association with one or more pharmaceutically-acceptable excipients. The quantity of active ingredient in a unit dose may be varied or adjusted from about 0.1 to about 1500 milligrams or more according to the particular treatment involved. It may be preferred that the unit dosage is from about 1 mg to about 1000 mg.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

Solid form formulations include powders, tablets and capsules.

Sterile liquid formulations include suspensions, emulsions, syrups, and elixirs.

Pharmaceutical compositions of the present invention can be manufactured in a manner that is itself known, e.g., by means of conventional mixing, dissolving, granulating, dragee-making, levigating, emulsifying, encapsulating, entrapping or lyophilizing processes.

The following pharmaceutical formulations 1 and 2 are illustrative only and are not intended to limit the scope of the invention in any way.

Formulation 1

Hard gelatin capsules are prepared using the following ingredients:

|  | Quantity (mg/capsule) |
| --- | --- |
| Active Ingredient | 250 |
| Starch, dried | 200 |
| Magnesium stearate | 10 |
| Total | 460 mg |

Formulation 2

A tablet is prepared using the ingredients below:

|  | Quantity (mg/tablet) |
| --- | --- |
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

The compounds of the present invention can be useful for modulating insulin secretion and as research tools. Certain compounds and conditions within the scope of this invention are preferred. The following conditions, invention embodiments, and compound characteristics listed in tabular form are preferred features and may be independently combined to produce a variety of preferred compounds and process conditions. The following list of embodiments of this invention is not intended to limit the scope of this invention in any way.

Some prefered characteristics of compounds of formula I are:

(a) R3 is methyl;
(b) R4 is hydrogen;
(c) R3 and R4 are each hydrogen;
(d) R3 and R4 are each methyl;
(e) A is carboxyl;
(f) X is —O—;
(g) X is —S—;
(h) X is a bond;
(i) U is CH;
(j) U is CH$_2$CH;
(k) U is substituted with arylC$_1$-C$_4$alkyl;
(l) R9 is methyl;
(m) R9 is hydrogen;
(n) R9 is C$_1$-C$_3$ alkyl;
(o) R8 is methyl;
(p) R8 and R9 are each hydrogen;

(q) R10 is $CF_3$;
(r) R10 is haloalkyl;
(s) R10 is haloalkyloxy;
(t) R11 is hydrogen;
(u) R10 and R11 are each hydrogen;
(v) R11 is haloalkyl;
(w) R1 is substituted $C_1$-$C_4$ alkyl;
(x) R1 is hydrogen;
(y) Y is O;
(z) Y is S;
(aa) Y is C;
(bb) E is C(R3)(R4)A;
(cc) R3 is hydrogen;
(dd) R3 is $C_1$-$C_2$ alkyl;
(ee) R4 is $C_1$-$C_2$ alkyl;
(ff) R4 is selected from the group consisting of alkoxy and aryloxy;
(gg) A is COOH;
(hh) Aliphatic linker is saturated;
(ii) Aliphatic linker is substituted with $C_1$-$C_3$ alkyl;
(jj) Aliphatic linker is substituted with aryl$C_1$-$C_4$alkyl;
(kk) Aliphatic linker is $C_1$-$C_3$ alkyl;
(ll) Aliphatic linker is $C_1$-$C_2$ alkyl;
(mm) Aliphatic linker is $C_1$-$C_3$ alkyl and one carbon is replaced with an —O—;
(nn) Aliphatic linker is $C_1$-$C_3$ alkyl and one carbon is replaced with an —S—;
(oo) Aryl is a phenyl group;
(pp) A compound of Formula I that selectively modulates a delta receptor;
(qq) An Active Ingredient, as described herein, that is a PPAR coagaonist that modulates a gamma receptor and a delta receptor;
(rr) An Active Ingredient, as described herein, for use in the treatment of cardiovascular disease;
(ss) An Active Ingredient, as described herein, for use in the treatment of Metabolic syndrome;
(tt) An Active Ingredient for use in the control of obesity;
(uu) An Active Ingredient for use in treating diabetes;
(vv) An Active Ingredient that is a PPAR receptor agonist;
(ww) A compound of Formula I wherein the headpiece of Formula I is:

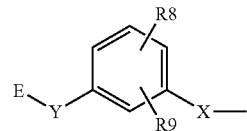

(xx) A compound of Formula I selected from the group consisting of (2-Methyl-4-{2-[3-methyl-5-(4-trifluoromethyl-phenyl)-thiophen-2-yl]-propylsulfanyl}-phenoxy)-acetic acid, (2-Methyl-4-{2-[3-methyl-5-(4-trifluoromethyl-phenyl)-thiophen-2-yl]-propylsulfanyl}-phenoxy)-acetic acid, 3-(2-Methyl-4-{2-[3-methyl-5-(4-trifluoromethyl-phenyl)-thiophen-2-yl]-propylsulfanyl}-phenyl)-propionic acid, and (3-{2-[3-Methyl-5-(4-trifluoromethyl-phenyl)-thiophen-2-yl]-propoxy}-phenyl)-acetic;
(yy) A compound of Formula I that is (3-{2-[3-Methyl-5-(4-trifluoromethyl-phenyl)-thiophen-2-yl]-propoxy}-phenyl)-acetic;
(zz) A compound of Formula I selected from the group consisting of:

| Compound | Name |
| --- | --- |
| ![structure] | 3-{2-Methyl-4-[5-(4-trifluoromethyl-phenyl)-thiophen-2-ylmethoxy]-phenyl}-propionic acid |
| ![structure] | {2-Methyl-4-[5-(4-trifluoromethyl-phenyl)-thiophen-2-ylmethoxy]-phenoxy}-acetic acid |
| ![structure] | 3-{2-Methyl-4-[3-phenyl-5-(4-trifluoromethyl-phenyl)-thiophen-2-ylmethoxy]-phenyl}-propionic acid |

| Compound | Name |
| --- | --- |
| (structure) | 3-{4-[3,5-Bis-(4-trifluoromethyl-phenyl)-thiophen-2-ylmethoxy]-2-methyl-phenyl}-propionic acid |
| (structure) | 3-(2-Methyl-4-{1-[3-methyl-5-(4-trifluoromethyl-phenyl)-thiophen-2-yl]-propoxy}-phenyl)-propionic acid |
| (structure) | 3-(2-Methyl-4-{1-[3-methyl-5-(4-trifluoromethyl-phenyl)-thiophen-2-yl]-butoxy}-phenyl)-propionic acid |
| (structure) | 3-(2-Methyl-4-{2-methyl-1-[3-methyl-5-(4-trifluoromethyl-phenyl)-thiophen-2-yl]-propoxy}-phenyl)-propionic acid |
| (structure) | 3-(2-Methyl-4-{1-[3-methyl-5-(4-trifluoromethyl-phenyl)-thiophen-2-yl]-2-phenyl-ethoxy}-phenyl)-propionic acid |
| (structure) | 3-(4-{1-[3-(2-Hydroxy-ethyl)-5-(4-trifluoromethyl-phenyl)-thiophen-2-yl]-ethylsulfanyl}-2-methyl-phenyl)-propionic acid |

SYNTHESIS

Compounds of the present invention have been formed as specifically described in the examples. Further, many compounds are prepared as more generally using a) alkylation of phenol/thiophenol with a halide, b) a Mitsunobu protocol (O. Mitsunobu, 1981 Synthesis, p1); c) and other methods known to the skilled artisan. Alternative synthesis methods may also be effective and known to the skilled artisan.

For example, an intermediate like A is alkylated with an alkylating agent B in the presence of a base (e.g. K2CO3, Cs2CO3 etc.). Hydrolysis in the presence of aqueous NaOH or LiOH gave the acid product.

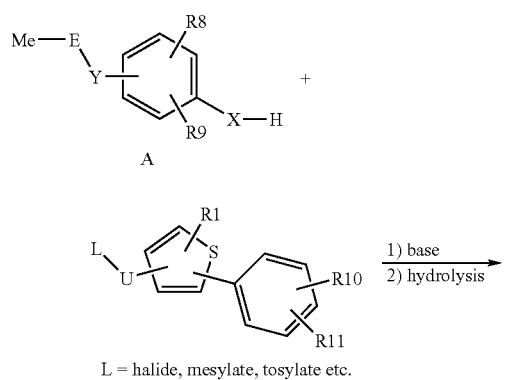

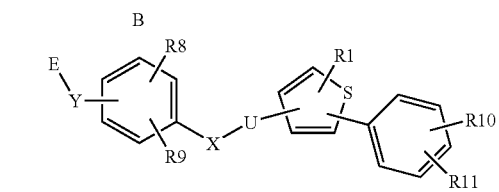

Alternatively, an intermediate like A is coupled with an alcohol C under Mitsunobu reaction condition (DEAD/PPh3, ADDP/Pbu3 etc.). Hydrolysis in the presence of aqueous NaOH or LiOH gave the acid product:

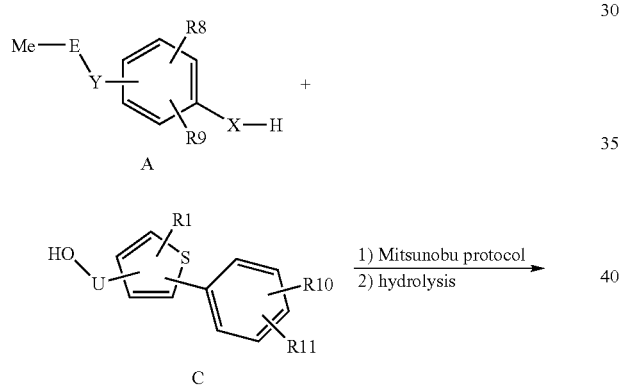

-continued

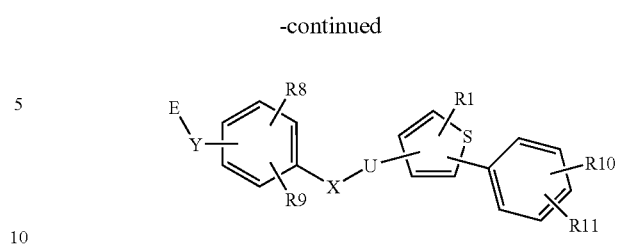

Thioether analogs could also be prepared by a ZnI2 mediated thioether formation reaction as shown below:

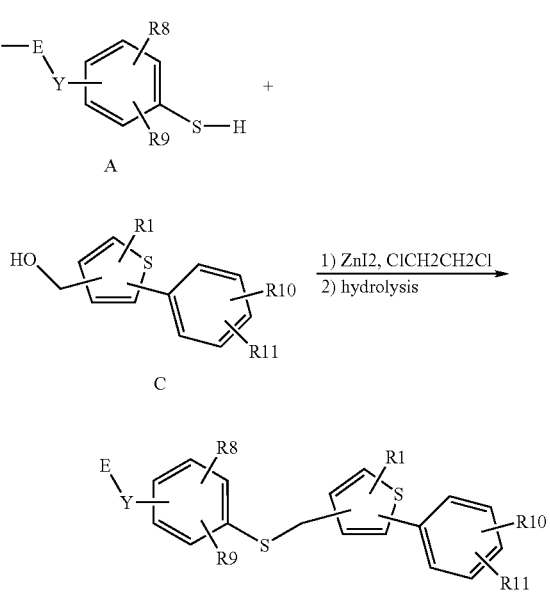

3-Substituted thiophene analogs can be made by the following schemes:

Scheme 1

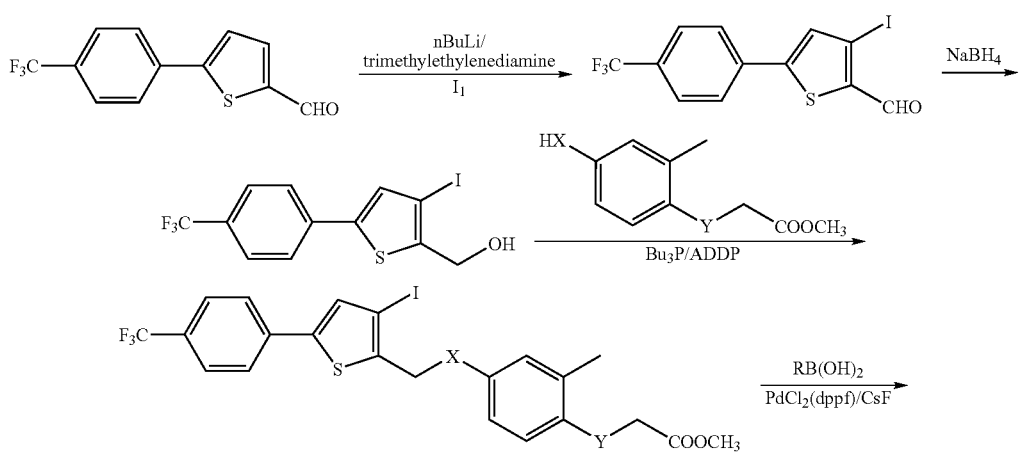

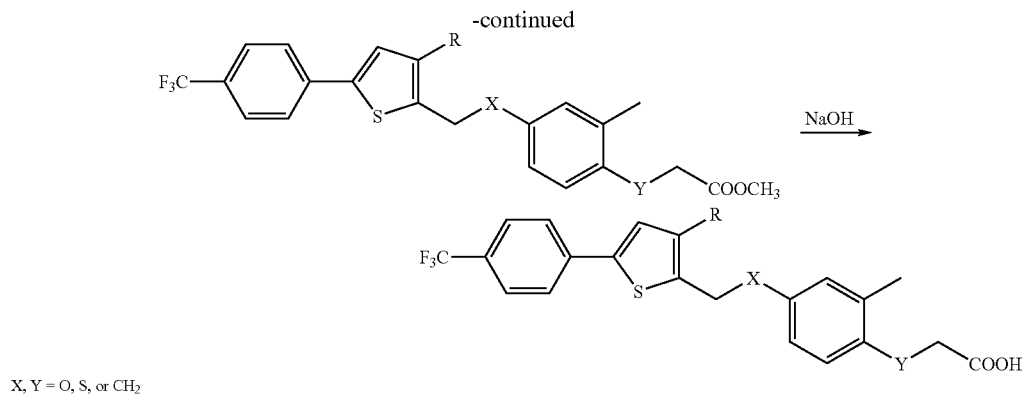
X, Y = O, S, or CH₂
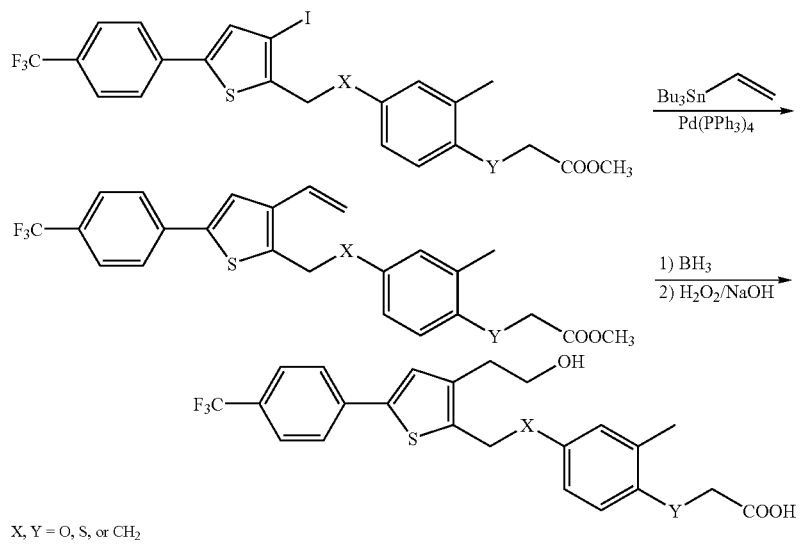
X, Y = O, S, or CH₂
Thiophene intermediates B and C can be made in one of the following methods:
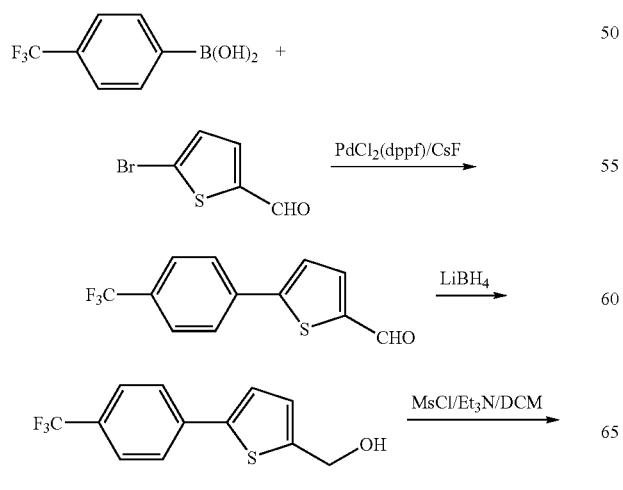
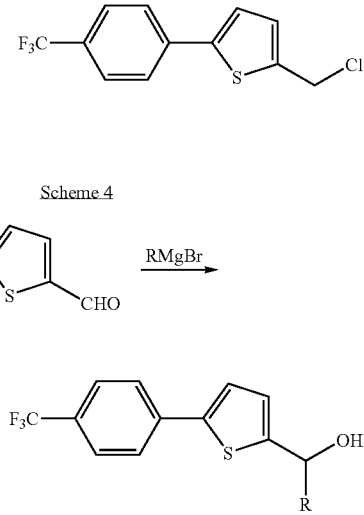

Scheme 5

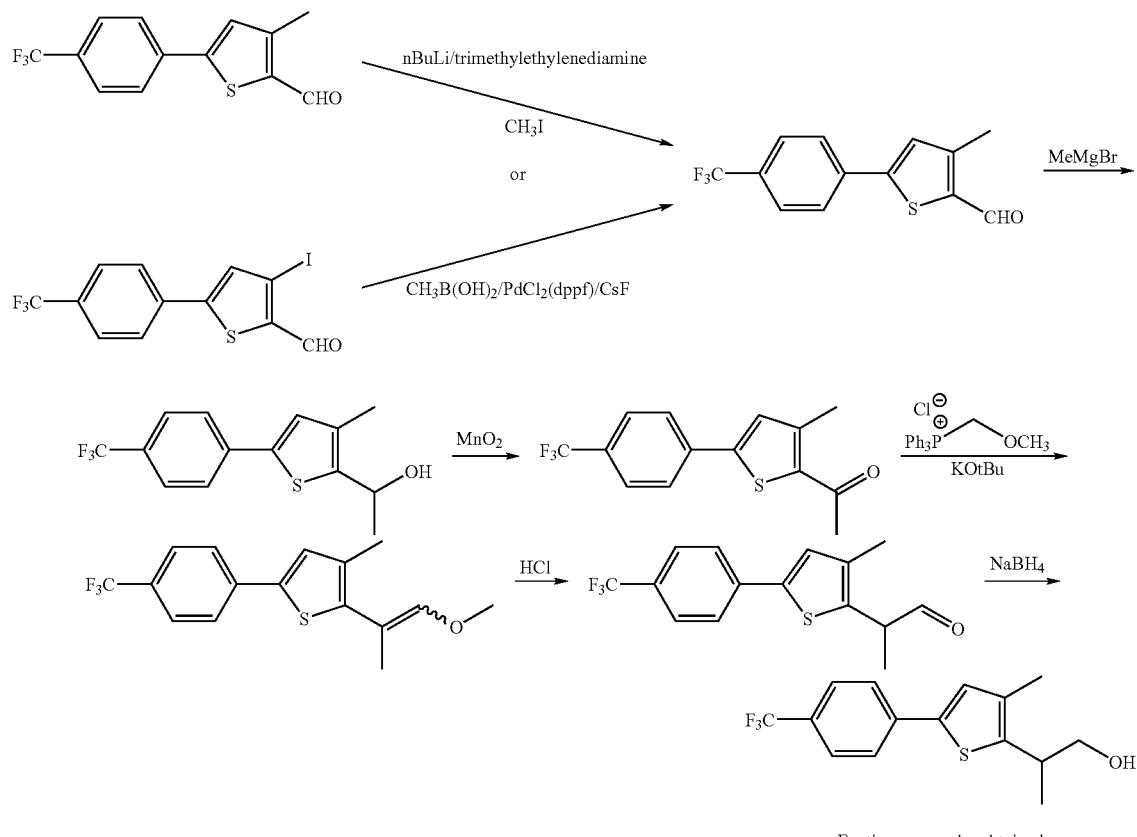

Enatiomers can be obtained by preparative Chiral HPLC

EXEMPLIFICATION

The Examples provided herein are illustrative of the invention claimed herein and are not intended to limit the scope of the claimed invention in any way.

Instrumental Analysis

Infrared spectra are recorded on a Perkin Elmer 781 spectrometer. $^1$H NMR spectra are recorded on a Varian 4.00 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses are performed by Eli Lilly & Company Microanalytical Laboratory. High resolution mass spectra are obtained on VG ZAB 3F or VG 70 SE spectrometers. Analytical thin layer chromatography is performed on EM Reagent 0.25 mm silica gel 60-F plates. Visualization is accomplished with UV light.

Preparation 1

2-(4-Hydroxy-2-methyl-phenoxy)-2-methyl-propionic acid

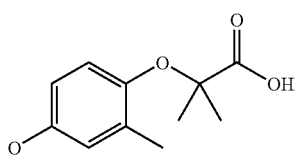

Step A 2-(4-Benzyloxy-2-formylphenoxy)-2-methyl propionic acid ethyl ester

5-Benzyloxy-2-hydroxy-benzaldehyde (Kappe, T.; Witoszynskyj, T. Arch. Pharm., 1975, 308 (5), 339-346) (2.28 g, 10.0 mmol), ethyl bromoisobutyrate (2.2 mL, 15 mmol), and cesium carbonate (3.26 g, 10.0 mmol) in dry DMF (25 mL) are heated at 80° C. for 18 h. The reaction mixture is cooled and partitioned between water (30 mL) and ether (75 mL). The organic layer is washed with brine (15 mL). The aqueous layers are back-extracted with ethyl acetate (30 mL), and the organic layer is washed with brine (20 mL). The combined organic layers are dried (Na$_2$SO$_4$) and concentrated to a brown oil. The crude product is purified by flash chromatography using hexanes:ethyl acetate (2.5:1) to give a pale yellow solid (3.04 g, 89%): mp 65° C.; $^1$H NMR (400 MHz, CDCl$_3$) δ 1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30-7.43 (m, 6H); MS (ES) m/e 343.1 [M+1].

Step B 2-(4-Hydroxy-2-methyl-phenoxy)-2-methyl-propionic acid ethyl ester 2-(4-Benzyloxy-2-formyl-phenoxy)-2-methyl-propionic acid ethyl ester (9.00 g, 26.3 mmol) in ethanol (250 mL) is treated with 5% Pd/C (1.25 g) and hydrogen (60 psi, rt, overnight). Additional 5% Pd/C (1.25 g) is added, and the reaction is continued for 6 h at 40° C. The mixture is filtered and concentrated to a tan oil (6.25 g). This oil contained 9 mol % of 2-(4-Hydroxy-2-hydroxymethyl-phenoxy)-2-methyl-propionic acid ethyl ester. $^1$H NMR (400 MHz, CDCl$_3$) δ 1.26 (t, 3H, J=7.3 Hz), 1.51 (s, 6H), 2.14 (s, 3H), 4.24 (q, 2H, J=7.3 Hz), 5.68 (brs, 1H), 6.47 (dd, 1H, J=3.4, 8.8 Hz), 6.59 (d, 1H, J=8.3 Hz), 6.60 (brs, 1H).

The following compound is prepared in a similar manner:

Preparation 2

2-(4-Hydroxy-2-methyl-phenoxy)-acetic acid

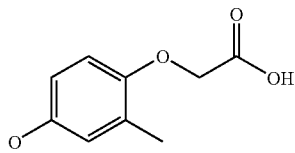

$^1$H NMR (400 MHz, CDCl3) δ 1.28 (t, 3H, J=7.1 Hz), 2.24 (s, 3H), 4.25 (q, 2H, J=7.1 Hz), 4.55 (s, 2H), 6.56 (dd, 1H, J=2.7, 8.5 Hz), 6.61 (d, 1H, J=8.3 Hz), 6.65 (d, 2H, J=2.9 Hz).

Preparation 3

(4-Hydroxy-2-propyl-phenoxy)-acetic acid ethyl ester

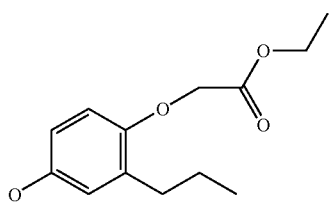

Step A

4-Benzyloxy-2-propylphenol

2-Allyl-4-benzyloxyphenol (WO 9728137 A1 19970807, Adams, A. D. et al.) (5.00 g, 20.8 mmol) in ethyl acetate (40 mL) is treated with 5% Pd/C (0.25 g) and hydrogen (1 atm) at ambient temperature for 18 h. The mixture is filtered and concentrated. The crude product is purified on a Biotage medium pressure chromatography system using a 40L normal phase cartridge and eluted with 10% ethyl acetate in hexanes to give a tan solid (2.8 g, 56%). Rf=0.33 (25% EtOAc/Hexanes); $^1$H NMR (400 MHz, CDCl$_3$) δ 7.44-7.31 (m, 5H), 6.78 (s, 1H), 6.69 (d, J=1.5 Hz, 2H), 5.00 (s, 2H), 4.31 (s, 1H), 2.55 (t, J=7.6 Hz, 2H), 1.64 (q, J=7.5 Hz, 2H), 0.97 (t, J=7.3 Hz, 3H).

Step B (4-Benzyloxy-2-propylphenoxy)acetic acid ethyl ester

A solution of 4-benzyloxy-2-propylphenol (0.50 g, 1.94 mmol) in dry DMF (7 mL) is cooled in an ice bath and treated with NaH (0.15 g, 3.8 mmol, 60% oil dispersion). The ice bath is removed, ethyl bromoacetate (0.43 mL, 3.9 mmol) is added, and the mixture is placed in an oil bath (T=85° C.). After 18 h, the reaction mixture is cooled and concentrated in vacuo. The residue is diluted with EtOAc, washed with brine (2×), dried (Na$_2$SO$_4$), and concentrated. The crude product is purified by radial chromatography using 10% ethyl acetate in hexanes to give a tan solid (0.62 g, 97%). $^1$H NMR (400 MHz, CDCl$_3$) δ 7.44-7.31 (m, 5H), 6.82 (d, J=2.9 Hz, 1H), 6.72 (dd, J=8.8, 2.9 Hz, 1H), 6.66 (d, J=8.8 Hz, 1H), 5.00 (s, 2H), 4.57 (s, 2H), 4.25 (q, J=7.0 Hz, 2H), 2.63 (t, J=7.6 Hz, 2H), 1.64 (q, J=7.5 Hz, 2H), 1.29 (t, J=7.1 Hz, 3H), 0.95 (t, J=7.3 Hz, 3H); MS (FIA) m/e 329 (M+1).

Step C (4-Hydroxy-2-propylphenoxy)acetic acid ethyl ester

A solution of (4-benzyloxy-2-propylphenoxy)acetic acid ethyl ester (0.60 g, 1.83 mmol) in THF (15 mL) is treated with 5% Pd/C (75 mg) and hydrogen (60 psi) at ambient temperature for 24 h. The mixture is filtered and concentrated. The crude product is purified by radial chromatography using 15% ethyl acetate in hexanes to give a tan solid (0.25 g, 57%). $^1$H NMR (400 MHz, CDCl$_3$) δ 6.66 (d, J=2.9 Hz, 1H), 6.62 (d, J=8.8 Hz, 1H), 6.57 (dd, J=8.8, 2.9 Hz, 1H), 4.56 (s, 1H), 4.40 (s, 1H), 4.25 (q, J=7.2 Hz, 2H), 2.61 (t, J=7.6 Hz, 2H), 1.63 (q, J=7.5 Hz, 2H), 1.29 (t, J=7.1 Hz, 3H), 0.95 (t, J=7.3 Hz, 3H); MS (FIA) m/e 239 (M+1).

Preparation 4

(3-Bromo-4-hydroxy-phenoxy)-acetic acid ethyl ester

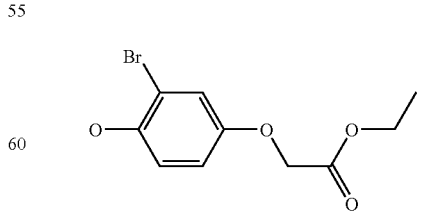

To a solution of (4-hydroxy-phenoxy)-acetic acid ethyl ester (0.59 g, 3 mmol) in acetic acid (1.5 mL) is added bromine (0.48 g, 9 mmol) in acetic acid (0.5 mL) at room temperature. After 5 min, solvent is evaporated and purified by column chromatography on silica gel giving the title compound (0.6 g).

Preparation 5

(4-Mercapto-phenoxy)-acetic acid ethyl ester

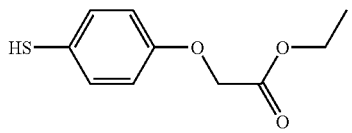

Step A (4-Chlorosulfonyl-phenoxy)-acetic acid ethyl ester

Phenoxy-acetic acid ethyl ester (9.1 mL) is added to chlorosulfonic acid (15 mL) at 0° C. dropwise. The reaction is stirred at 0° C. for 30 min, it is allowed to warm to room temperature. After 2 hrs, the reaction mixture is poured into ice, solid product is collected by filtration and dried under vacuum.

Step B (4-Mercapto-phenoxy)-acetic acid ethyl ester

To a mixture of (4-chlorosulfonyl-phenoxy)-acetic acid ethyl ester (0.98 g, 3.5 mmol) and tin powder (2.1 g) in ethanol (4.4 mL) is added HCl in dioxane (1.0 M, 4.4 mL) under nitrogen. The mixture is heated to reflux for 2 hrs, it is poured into ice and methylene chloride and filtered. The layers are separated and extracted with methylene chloride, dried and concentrated. The crude product is used for next step without purification.

The following compounds are made in a similar manner:

Preparation 6

(4-Mercapto-2-methyl-phenoxy)-acetic acid ethyl ester

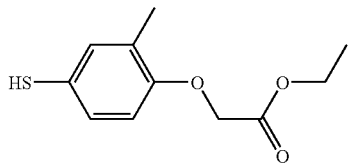

This compound can also be made by the following procedure:

To a stirred suspension of Zn powder (10 μm, 78.16 g, 1.2 mol) and dichlorodimethyl silane (154.30 g, 145.02 mL, 1.2 mol) in 500 mL of dichloroethane is added a solution of (4-chlorosulfonyl-2-methyl-phenoxy)-acetic acid ethyl ester (100 g, 0.34 mol) and 1,3-dimethylimidazolidin-2-one (116.98 g, 112.05 mL, 1.02 mol) in 1 L of DCE. Addition is at a rate so as to maintain the internal temperature at ~52° C., cooling with chilled water as necessary. After addition is complete, the mixture is heated at 75° C. for 1 hour. It is then cooled to room temperature, filtered and concentrated iv. Add MTBE, washed twice with saturated LiCl solution, concentrate iv again. Take up the residue in $CH_3CN$, wash with hexane (4×) and concentrate iv to yield a biphasic mixture. Let stand in a separatory funnel and separate layers, keeping the bottom layer for product. Filtration through a plug of silica gel (1 Kg, 25% EtOAc/hexane) and subsequent concentration yields 61 g (79%) of a clear, colorless oil.

NMR (DMSO-$d_6$) δ 7.1 (s, 1H), 7.05 (dd, 1H), 6.75 (d, 1H), 5.03 (s, 1H), 4.75 (s, 2H), 4.15 (q, 2H), 2.15 (s, 3H), 1.2 (t, 3H).

Preparation 7

(4-Mercapto-2-propyl-phenoxy)-acetic acid ethyl ester

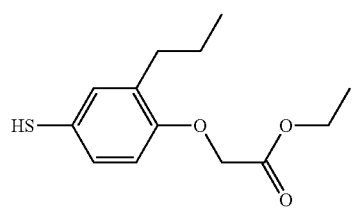

Preparation 8

3-(4-Hydroxy-2-methyl-phenyl)-propionic acid methyl ester

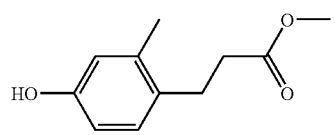

Step A

4-Bromo-3-methyl-phenyl benzyl ester

To a solution of 4-Bromo-3-methyl-phenol (20.6 g, 0.0.11 mol) in DMF (100 mL) is added Cs2CO3 (54 g, 0.165 mol), followed by benzyl bromide (14.4 mL). After stirred at 60° C. for 40 h, the reaction mixture is diluted with ethyl acetate, filtered through celite. The filtrate is washed with water and brine, dried over sodium sulfate, concentration yields the title product (27 g).

Step B 3-(4-Benzyloxy-2-methyl-phenyl)-propionic acid methyl ester

To a solution of 4-bromo-3-methyl-phenyl benzyl ester (7.6 g, 27.4 mmol) in propronitrile (200 mL) is added methyl acrylate (10 mL) and diisopropylethyl amine (9.75 mL), the solution is degassed and filled with nitrogen for three times. To this mixture are added tri-o-tolyl-phosphane (3.36 g) and palladium acetate (1.25 g) under nitrogen, then heated at 110° C. overnight, cooled to room temperature, filtered through celite. The solvent is evaporated, the residue is taken into ethyl acetate and washed with water and brine, dried over sodium sulfate. Concentration and column chromatography on silica gel eluted with hexanes and ethyl acetate yields the title compound (6.33 g).

Step C

3-(4-Hydroxy-2-methyl-phenyl)-propionic acid methyl ester

A mixture of 3-(4-Benzyloxy-2-methyl-phenyl)-propionic acid methyl ester (13.7 g, 48.5 mmol) and Pd/C (5%, 13.7 g) in MeOH (423 mL) is stirred under 60 psi of hydrogen for 24 hrs. Catalyst is filtered off, filtrate is concentrated giving the title compound (8.8 g, 93.5%).

Preparation 9

3-(4-Mercapto-2-methyl-phenyl)-propionic acid methyl ester

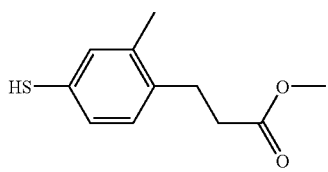

Step A

3-(4-Dimethylthiocarbamoyloxy-2-methyl-phenyl)-propionic acid methyl ester 3-(4-Hydroxy-2-methyl-phenyl)-propionic acid methyl ester (5.0 g, 25.75 mmol) is dissolved into dry dioxane (100 mL) and combined with 4-dimethylamino pyridine (0.500 g, 2.6 mmol), triethylamine (7.0 mL, 51.5 mmol), and dimethylaminothiocarbomoyl chloride (4.5 g, 32.17 mmol). The reaction is heated to reflux under nitrogen. The reaction is monitored by TLC until all of the phenol is consumed, 20 h. After cooling to room-temperature, the reaction is diluted with ethyl acetate (200 mL). Water (75 mL) is added and the two layers are separated. The organic layer is washed with brine (75 mL) then dried over anhydrous sodium sulfate. The solvent is removed and the residue is dried under vacuum.

Step B

3-(4-Dimethylcarbamoylsulfanyl-2-methyl-phenyl)-propionic acid methyl ester 3-(4-Dimethylthiocarbamoyloxy-2-methyl-phenyl)-propionic acid methyl ester, taken crude from the previous step, is diluted with 75 mL of tetradecane and heated to reflux under nitrogen. The reaction is monitored by TLC until all the conversion is complete, 20 h. The reaction is allowed to cool to room temperature, then the tetradecane is decanted away from the resulting oil. The residue is rinsed several times with hexanes. This oil is then purified using flash column chromatography, yielding 5.01 g, or 69% (2 steps) of the product.

Step C

3-(4-Mercapto-2-methyl-phenyl)-propionic acid methyl ester 3-(4-Dimethylcarbamoylsulfanyl-2-methyl-phenyl)-propionic acid methyl ester (5.01 g, 17.8 mmol) is diluted with methanol (30 mL) and to this is added sodium methoxide (1.7 mL of 4M in methanol, 7.23 mmol). The reaction is heated to reflux under nitrogen and monitored by TLC. After complete conversion, 20 h., the reaction is allowed to cool to room temperature. The reaction is neutralized with 1N HCl (7.23 mL) and diluted with ethyl acetate (150 mL). The two phases are separated and the organic layer is washed with water (75 mL), then brine (75 mL). The organic layer is then dried over anhydrous sodium sulfate, then concentrated to yield 4.43 g crude product that is used without further purification.

Preparation 10

4-(2-Methoxycarbonyl-ethyl)-3-methyl-benzoic acid

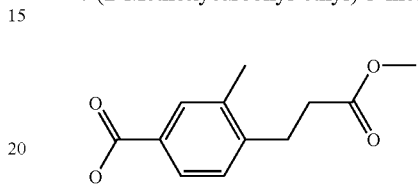

Step A

4-Bromo-3-methyl-benzoic acid benzyl ester

To a solution of 4-Bromo-3-methyl-benzoic acid benzyl (25.3 g, 0.118 mol) in DMF (200 mL) is added Cs2CO3 (76.6 g, 0.235 mol), followed by benzyl bromide (15.4 mL). After stirred at room temperature for 2 h, the reaction mixture is diluted with ethyl acetate, filtered through celite. The filtrate is washed with water and brine, dried over sodium sulfate, concentration yields the title product.

Step B

4-(2-Methoxycarbonyl-vinyl)-3-methyl-benzoic acid benzyl ester

To a solution of 4-bromo-3-methyl-benzoic acid benzyl ester (36 g, 118 mmol) in propronitrile (1000 mL) is added methyl acrylate (43.3 mL) and diisopropylethyl amine (42 mL), the solution is degassed and filled with nitrogen for three times. To this mixture are added tri-o-tolyl-phosphane (14.5 g) and palladium acetate (5.34 g) under nitrogen, then heated at 110° C. overnight, cooled to room temperature, filtered through celite. The solvent is evaporated, the residue is taken into ethyl acetate and washed with water and brine, dried over sodium sulfate. Concentration and column chromatography on silica gel eluted with hexanes and ethyl acetate yields the title compound (31 g, 84.7%).

Step C

4-(2-Methoxycarbonyl-ethyl)-3-methyl-benzoic acid

A mixture of 4-(2-methoxycarbonyl-vinyl)-3-methyl-benzoic acid benzyl ester (11.6 g, 37.4 mmol) and Pd/C (5%, 1.5 g) in THF (300 mL) and methanol (100 mL) is stirred under 60 psi of hydrogen overnight. Catalyst is filtered off, filtrate is concentrated giving the title compound (8.3 g, 100%).

Preparation 11

(4-Hydroxy-2-methyl-phenyl)-acetic acid methyl ester

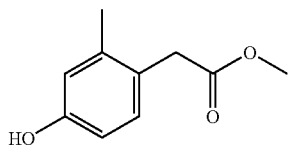

Step A

4-Methoxy-2-methylbenzoic acid (2.5 g, 15.04 mmol) is stirred in thionyl chloride (50 mL) at reflux 2 hr. The mixture is concentrated and diluted with toluene (10 mL) and concentrated. The resulting solid is dried under vacuum 18 hr. The resulting acid chloride is stirred in 20 mL ether at 0 deg C. A solution of diazomethane (39.6 mmol) in ether (150 mL) is added to the acid chloride solution and stirred 18 hr. The resulting diazoketone solution is concentrated. The residue is stirred in methanol (100 mL) and a solution of silver benzoate in triethylamine (1.0 g in 10 mL) is added and the reaction is heated to 60 deg C. and stirred 1 hr. The mixture is concentrated, diluted with 1.0 N aqueous hydrochloric acid (20 mL), extracted to three portions of ethyl acetate (50 mL each). The extracts are combined, washed with aqueous saturated sodium hydrogen carbonate, water, and brine (50 mL each), dried over anhydrous magnesium sulfate, filtered and concentrated. The residue is purified via silica gel chromatography eluting with 9:1 hexanes:ethyl acetate to afford 1.5 g (51%) of the homologated ester as a white solid.

Step B (4-Methoxy-2-methyl-phenyl)-acetic acid methyl ester (1.5 g, 7.72 mmol) is stirred in dichloromethane (50 mL) at 0 deg. C. Aluminum chloride (4.13 g, 31 mmol) is added followed by ethane thiol (2.9 mL, 38.6 mmol). The resulting mixture is stirred at room temperature for 2 hr. Water (50 mL) is added and the product is extracted into ethyl acetate (3×50 ml), the extracts are combined, dried over anhydrous magnesium sulfate, filtered, and concentrated to afford the title compound as a colorless oil, 1.4 g, 100%. MS M$^+$+1 181. The structure is confirmed by $^1$H NMR spectroscopy.

Preparation 12

(3-Hydroxy-phenyl)-acetic acid methyl ester

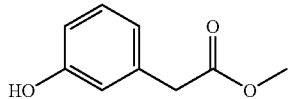

Step A (3-Hydroxy-phenyl)-acetic acid methyl ester (3-Hydroxy-phenyl)-acetic acid (5.0 g, 32.86 mmol) is stirred in methanol (100 mL) and concentrated (98%) sulfuric acid (3.0 mL,) is added. The mixture is heated to reflux 18 hr. The reaction is cooled and concentrated. The residue is diluted with water (100 mL) and extracted with ethyl acetate (3×50 mL). The combined extracts are dried over anhydrous magnesium sulfate, filtered, and concentrated to yield the title compound as an orange oil, 5.46 g, 100%. MS M$^+$+1 167. The structure is confirmed by $^1$H NMR spectroscopy.

The following compounds are made in a similar manner:

Preparation 13

(3-Hydroxy-4-methoxy-phenyl)-acetic acid methyl ester

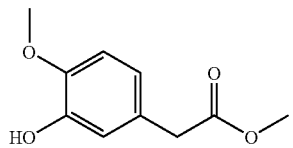

An orange oil. MS M$^+$+1 197. The structure is confirmed by $^1$H NMR spectroscopy.

Preparation 14

3-(3-Hydroxy-phenyl)-propionic acid methyl ester

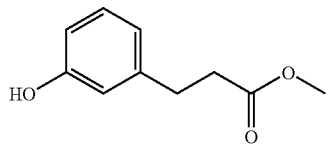

Step A 3-(3-Hydroxy-phenyl)-propionic acid methyl ester

An orange oil. MS M$^+$+1 181. The structure is confirmed by $^1$H NMR spectroscopy.

Preparation 15

(3-Mercapto-phenyl)-acetic acid methyl ester

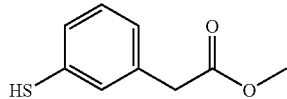

Step A (3-Dimethylthiocarbamoyloxy-phenyl)-acetic acid methyl ester

A mixture of (3-Hydroxy-phenyl)-acetic acid methyl ester (5.5 g, 33.1 mmol), N,N-dimethyl thiocarbamoyl chloride (5.11 g, 41.38 mmol), triethylamine (9.2 mL, 66.2 mmol), N,N-dimethylamino pyridine (0.4 g, 3.31 mmol) and dioxane (50 mL) is stirred at reflux 18 hr. The mixture is concentrated, partioned between 1M aqueous hydrochloric acid (200 mL) and ethyl acetate (3×75 mL). The combined organic extracts are dried over anhydrous magnesium sulfate, filtered, concentrated, and purified via silica chromatography eluting the product with dichloromethane to afford the title compound as a brown oil, 6.8 g, 81%. MS M$^+$+1 254. The structure is confirmed by $^1$H NMR spectroscopy.

Step B (3-Dimethylcarbamoylsulfanyl-phenyl)-acetic acid methyl ester (3-Dimethylthiocarbamoyloxy-phenyl)-acetic acid methyl ester (6.8 g, 26.84 mmol) is stirred in tetradecane (30 mL) at 255 deg C. for 8 hr. The mixture is cooled, the residue is purified by silica chromatography eluting the product with hexanes to 1:1 hexanes:ethyl acetate to afford the title compound as an orange oil, 4.9 g, 58%. MS M$^+$+1 254. The structure is confirmed by $^1$H NMR spectroscopy.

Step C (3-Mercapto-phenyl)-acetic acid methyl ester

A mixture of (3-dimethylcarbamoylsulfanyl-phenyl)-acetic acid methyl ester (2.0 g., 7.9 mmol), potassium hydroxide (1.4 g, 24 mmol), methanol (50 mL), and water (5 mL) is stirred at reflux 3 hr. The mixture is concentrated, and product partitioned between 1M aqueous hydrochloric acid (50 mL) and ethyl acetate (3×75 mL). The combined extracts are dried over anhydrous magnesium sulfate, filtered and concentrated. The residue is taken up in methanol (50 mL), 2 mL concentrated sulfuric acid is added, and the mixture refluxed 3 hr. The mixture is concentrated, and the residue purified by silica chromatography eluting with 7:3 hexanes:ethyl acetate to afford the title compound as a pale yellow oil, 1.0 g, 69%. MS M$^+$+1 183. The structure is confirmed by $^1$H NMR spectroscopy.

Preparation 16

3-(4-Iodomethyl-2-methyl-phenyl)-propionic acid methyl ester

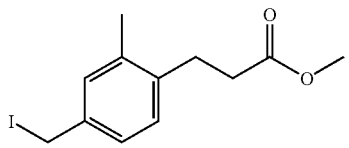

Step A 3-(4-Hydroxymethyl-2-methyl-phenyl)-acrylic acid methyl ester

A mixture of methyl-4-bromo-3-methylbenzoate (5.7 g, 24.88 mmol), lithium aluminum hydride (29 mL, 29 mmol, 1 M solution in tetrahydrofuran) and tetrahydrofuran (100 mL) is stirred in ice/water for 1 hr. The reaction is quenched with aqueous hydrochloric acid (50 mL, 1 M). The product is extracted into ethyl acetate (3×100 mL). The combined extracts are dried over anhydrous magnesium sulfate, filtered and concentrated. The crude product is taken up in propionitrile (100 mL). Methylacrylate (10 mL, 121.5 mmol), palladium acetate (1.12 g, 5 mmol), tri-o-tolylphosphine (3.0 g, 10 mmol), and N,N-diisopropyl ethylamine (8.7 mL, 50 mmol) are sequentially added and the resulting reaction mixture is heated to 110 deg C. 3 hr. The mixture is concentrated, and the residue diluted with aqueous hydrochloric acid (100 mL, 1M). The product is extracted with dichloromethane (2×100 mL) and ethyl acetate (100 mL). The combined extracts are dried over anhydrous magnesium sulfate, filtered, concentrated, and purified via silica chromatography eluting with 7:3 hexanes:ethyl acetate to 1:1 hexanes:ethyl acetate to afford the pure product as a yellow oil, 4.7 g, 91%. MS M$^+$+1 207. The structure is confirmed by $^1$H NMR spectroscopy.

Step B 3-(4-Hydroxymethyl-2-methyl-phenyl)-propionic acid methyl ester

A mixture of 3-(4-Hydroxymethyl-2-methyl-phenyl)-acrylic acid methyl ester (4.7 g, 22.8 mmol), Raney nickel (0.668 g) and tetrahydrofuran (618 mL) is shaken under 60 psig. Hydrogen 24 hr. The catalyst is filtered off, and the mixture is concentrated to afford the product as a pale yellow oil, 4.3 g, 91%. The structure is confirmed by $^1$H NMR spectroscopy.

Step C 3-(4-Iodomethyl-2-methyl-phenyl)-propionic acid methyl ester

A mixture of 3-(4-Hydroxymethyl-2-methyl-phenyl)-propionic acid methyl ester (0.62 g, 2.98 mmol), triphenyl phosphine (0.86 g, 3.27 mmol) and dichloromethane (10 mL) is stirred at room temperature. A solution of iodine (0.83 g, 3.27 mmol) in benzene (5 mL) is added and the black mixture is stirred at room temperature 2 hr. The brown mixture is diluted with 10% aqueous sodium hydrogen sulfite (5 mL) and the resulting clear mixture is washed with ethyl acetate (3×50 mL). The combined extracts are dried over anhydrous magnesium sulfate, filtered and concentrated. The residue is purified via silica chromatography eluting with 9:1 hexanes:ethyl acetate to afford the title compound as a crystalline ivory solid, 0.68 g, 72%. MS M$^+$+1 319. The structure is confirmed by $^1$H NMR spectroscopy.

Preparation 17

(4-Bromo-2-methyl-phenoxy)-acetic acid methyl ester

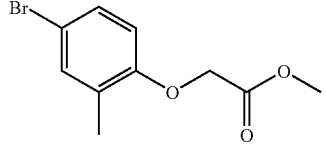

Step A (4-Bromo-2-methyl-phenoxy)-acetic acid methyl ester

A mixture of 4-bromo-2-methylphenol (1.0 g, 5.35 mmol), sodium hydride (0.26 g, 6.42 mmol, 60% mineral oil), N,N-dimethylformamide (10 mL), and methyl-2-bromoacetate (0.56 mL, 5.88 mmol) is stirred at room temperature 18 hr. The mixture is diluted with water (50 mL) and the product extracted to ethyl acetate (3×50 mL). The combined extracts are dried over anhydrous magnesium sulfate, filtered, concentrated and purified via silica chromatography eluting with 8:2 hexanes:ethyl acetate to afford title compound as a colorless oil, 1.03 g, 74%. MS M+ 259. The structure is confirmed by $^1$H NMR spectroscopy.

Preparation 18

3-(4-Amino-2-methyl-phenyl)-propionic acid methyl ester

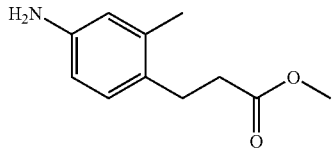

Step A 3-(2-Methyl-4-nitro-phenyl)-acrylic acid methyl ester

To a solution of 2-bromo-5-nitrotoluene (3.11 g, 14.39 mmol) in propionitrile (105 mL) is added DIPEA (5.1 mL, 29.28 mmol). The mixture is degassed three times. Methyl acrylate (5.2 mL, 57.74 mmol) is added and the mixture is degassed. Tri-o-tolylphosphine (1.77 g, 5.82 mmol) and Pd(OAc)$_2$ (0.64 g, 2.85 mmol) are added and the mixture is degassed a final two times followed by heating at 110° C. for 4 h. Upon cooling, the mixture is passed through Celite and the filtrate is concentrated. The residue is partitioned between Et$_2$O and 1N HCl. The organics are washed with saturated NaHCO$_3$ and brine, and dried with Na$_2$SO$_4$. The crude material is purified by flash chromatography to yield the title compound (2.90 g, 91%).

Step B 3-(4-Amino-2-methyl-phenyl)-propionic acid methyl ester

A mixture of 3-(2-Methyl-4-nitro-phenyl)-acrylic acid methyl ester (1.47 g, 6.64 mmol) and 5% Pd/C (0.29 g) in MeOH (100 mL) is exposed to a hydrogen atmosphere (60 psi) for 12 h. The mixture is filtered through Celite and purified by flash chromatography to yield the title compound (0.99 g, 77%).

Preparation 19

3-(2-Methyl-4-methylaminomethyl-phenyl)-propionic acid methyl ester TFA salt

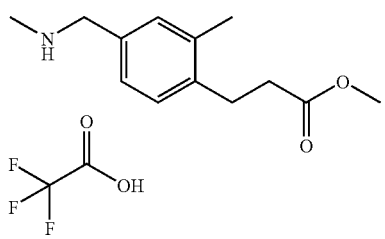

Step A 3-(4-Formyl-2-methyl-phenyl)-propionic acid methyl ester

A mixture of 3-(4-Hydroxymethyl-2-methyl-phenyl)-propionic acid methyl ester (0.49 g, 2.35 mmol) and MnO$_2$ (0.80 g, 9.20 mmol) in chloroform (5 mL) is stirred at RT for 4 days. The mixture is filtered through Celite; the Celite is washed with copious amounts of EtOAc. The filtrate is concentrated and purified by flash chromatography to yield the title compound (0.29.g, 60%).

Step B 3-(2-Methyl-4-methylaminomethyl-phenyl)-propionic acid methyl ester trifluoroacetic acid To a mixture of 3-(4-Formyl-2-methyl-phenyl)-propionic acid methyl ester (0.27 g, 1.31 mmol) and methylamine (2M in THF, 0.60 mL, 1.20 mmol) in anhydrous CH$_2$Cl$_2$ (10 mL) is added 4 Å molecular sieves followed by acetic acid (0.090 mL, 1.57 mmol). The mixture is stirred at RT for 1.5 h. Sodium triacetoxyborohydride (0.39 g, 1.85 mmol) is added, and the mixture is stirred overnight. The reaction is quenched with saturated NaHCO$_3$. The organics are washed with saturated NaHCO$_3$ and brine, and dried with MgSO$_4$. Upon concentration, the mixture is purified by reverse phase chromatography to yield the title compound (0.12 g, 45%).

Preparation 20

3-(4-Aminomethyl-2-methyl-phenyl)-propionic acid methyl ester

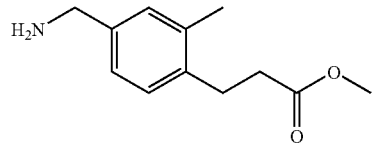

Step A 3-(4-Chloromethyl-2-methyl-phenyl)-propionic acid methyl ester

To a 0° C. solution of 3-(4-Hydroxymethyl-2-methyl-phenyl)-propionic acid methyl ester (1.02 g, 4.90 mmol) in anhydrous CH$_2$Cl$_2$ (15 mL) is added triethylamine (0.75 mL, 5.38 mmol) followed by thionyl chloride (0.40 mL, 5.48 mmol). The mixture is allowed to warm to RT overnight. Water is added, and the mixture is extracted with CH$_2$Cl$_2$. The organics are dried with MgSO$_4$ and concentrated. The crude material is purified by flash chromatography to yield the title compound (1.01 g, 91%).

Step B 3-(4-Azidomethyl-2-methyl-phenyl)-propionic acid methyl ester

To a solution of 3-(4-Chloromethyl-2-methyl-phenyl)-propionic acid methyl ester (0.52 g, 2.31 mmol) in DMF (7 mL) is added sodium azide (0.25 g, 3.84 mmol). The mixture is stirred overnight. Water is added, and the mixture is extracted with EtOAc. The organics are dried with Na$_2$SO$_4$ and concentrated to yield the title compound (0.49 g, 91%). The material is used without further purification.

Step C 3-(4-Aminomethyl-2-methyl-phenyl)-propionic acid methyl ester

A mixture of 3-(4-Azidomethyl-2-methyl-phenyl)-propionic acid methyl ester (0.20 g, 0.86 mmol) and 5% Pd/C (32 mg) in EtOH (50 mL) is exposed to a hydrogen atmosphere (60 psi) at RT overnight. Upon filtering the mixture through Celite, the filtrate is concentrated to yield the title compound (0.14 g, 78%). The material is used without further purification.

Preparation 21

2-Chloromethyl-5-(4-trifluoromethyl-phenyl)-thiophene

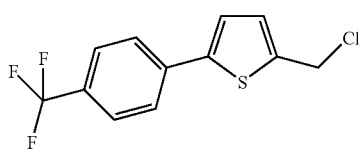

Step A 5-(4-Trifluoromethyl-phenyl)-thiophene-2-carbaldehyde

To a mixture of 4-(trifluoromethyl)phenyl-boronic acid (5.18 g, 27.3 mmole), 5-bromo-2-thiophenecarboxyaldehyde (5.39 g, 27.3 mmole) and cesium fluoride (14.5 g, 95.5 mmole) in dioxane (100 mL), is bubbled with nitrogen gas for 15 minutes. The catalyst $PdCl_2$ (dppf) (0.52 g) is then added to the mixture. The reaction is heated under reflux for 16 hours. The solvent is removed on rota vapor, and the resulting residue is partitioned between ethyl acetate (500 ml) and water (500 mL). The aqueous layer is extracted with more ethyl acetate (100 mL). The combined organic solution is washed with brine (3×500 mL), dried over $Na_2SO_4$ and concentrated. The crude product is purified on a silica gel column, eluting with 0-15% ethyl acetate in hexane and concentrated to provide the titled compound as yellow solid.

Step B

[5-(4-Trifluoromethyl-phenyl)-thiophen-2-yl]-methanol

To a solution of 5-(4-Trifluoromethyl-phenyl)-thiophene-2-carbaldehyde (3.02 g, 11.8 mmole) in THF (100 mL), is added to $LiBH_4$ (1.75 g, 80.24 mmole) in one portion at 0° C. The reaction is kept at 0° C. for 15 minutes and warmed up to room temperature for 1 hour. The reaction is quenched using 5N HCl (100 mL) at 0° C. The THF is removed on rota vapor, the aqueous solution is then extracted with ethyl acetate (2×100 mL). The combined organic solution is washed with brine (3×200 mL), dried over $Na_2SO_4$ and concentrated. The crude product is purified on a silica gel column, eluting with 20% ethyl acetate in hexane and concentrated to provide the titled compound as off-white solid.

Step C

2-Chloromethyl-5-(4-trifluoromethyl-phenyl)-thiophene

To a mixture of [5-(4-Trifluoromethyl-phenyl)-thiophen-2-yl]-methanol (1.52 g, 5.89 mmole) and triethyl amine (1.64 mL, 11.78 mmole) in DCM (100 mL) at 0° C., is injected methanesulfonyl chloride (0.91 mL, 11.78 mmole) dropwise. The reaction is kept at 0° C. for an hour and warmed up to room temperature for an hour. The reaction mixture is concentrated on rota vapor, and the resulting residue is purified on a silica gel column, eluting with 0-15% ethyl acetate in hexane and concentrated to provide the titled compound as off-white solid.

Preparation 22

[5-(4-Trifluoromethyl-phenyl)-thiophen-2-yl]-methanol

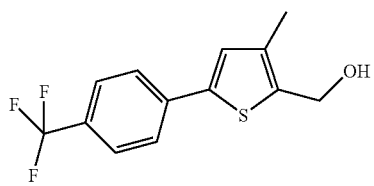

Step A

3-Methyl-5-(4-trifluoromethyl-phenyl)-thiophene-2-carbaldehyde

To a solution of trimethylethylenediamine (0.296 mL, 2.28 mmole) in THF at −78° C., is injected 2.0M n-butyllithium in cyclohexane (1.14 mL, 2.28 mmole) dropwise. The mixture is stirred for 15 minutes, then added a solution of 5-(4-Trifluoromethyl-phenyl)-thiophene-2-carbaldehyde (0.530 g, 2.07 mmole) in THF (5 mL) and stirred for another 15 minutes. To the resulting mixture is injected 2.0M n-butyllithium in cyclohexane (1.55 ml, 3.10 mmole) at −78° C. and warmed up to −18° C. for an hour. The reaction is cooled down to −78° C. again, quenched with excess amount of iodomethane (0.644 mL, 10.35 mmole) and allowed to warm up to room temperature, then poured into well stirred ice-water (30 mL). The aqueous solution is then extracted with ethyl acetate (2×30 mL). The combined organic solution is washed with brine (3×30 mL), dried over $Na_2SO_4$ and concentrated. The crude product is purified on a silica gel column, gradient eluting with 0-20% ethyl acetate in hexane and concentrated to provide the titled compound as yellow crystalline.

Step B

To a solution of 3-methyl-5-(4-Trifluoromethyl-phenyl)-thiophene-2-carbaldehyde (0.140 g, 0.518 mmole) in THF (5 mL), is added to $LiBH_4$ (0.056 g, 2.57 mmole) in one portion at 0° C. The reaction is kept at 0° C. for 15 minutes and warmed up to room temperature for 1 hour. The reaction is quenched using 1N HCl (10 mL) at 0° C. The THF is removed on rota vapor, the aqueous solution is then extracted with ethyl acetate (2×10 mL). The combined organic solution is washed with brine (3×20 mL), dried over $Na_2SO_4$ and concentrated. The crude product is purified on a silica gel column, eluting with 20% ethyl acetate in hexane and concentrated to provide the titled compound as white solid.

Preparation 23

1-[3-Methyl-5-(4-trifluoromethyl-phenyl)-thiophen-2-yl]-ethanol

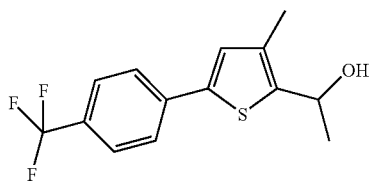

To a solution of 3-methyl-5-(4-Trifluoromethyl-phenyl)-thiophene-2-carbaldehyde (0.130 g, 0.481 mmole) in THF (5 mL), is injected 3.0 M MeMgBr in ethyl ether (0.27 mL, 0.810 mmole) dropwise. The reaction is stirred for 2 hours. The reaction is quenched with saturated $NH_4Cl_{(aq)}$ (10 mL), then the aqueous solution is extracted with ethyl acetate (3×15 mL). The combined organic solution is washed with brine (3×50 mL), dried over $Na_2SO_4$ and concentrated. The crude product is purified on a silica gel column, eluting with 0-20% ethyl acetate in hexane and concentrated to provide the titled compound as yellow solid.

The following compounds are made in a similar manner:

Preparation 24

[3-Iodo-5-(4-trifluoromethyl-phenyl)-thiophen-2-yl]-methanol

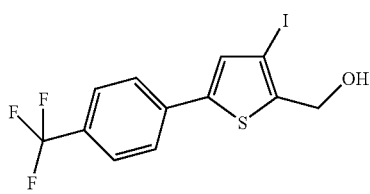

Preparation 25

1-[3-Iodo-5-(4-trifluoromethyl-phenyl)-thiophen-2-yl]-ethanol

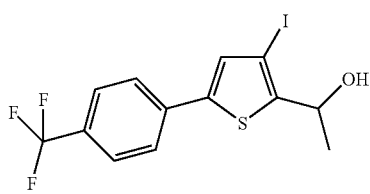

Preparation 26

1-[3-Methyl-5-(4-trifluoromethyl-phenyl)-thiophen-2-yl]-propan-1-ol

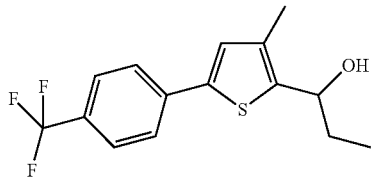

Preparation 27

1-[3-Methyl-5-(4-trifluoromethyl-phenyl)-thiophen-2-yl]-butan-1-ol

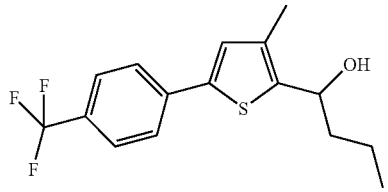

Preparation 28

2-Methyl-1-[3-methyl-5-(4-trifluoromethyl-phenyl)-thiophen-2-yl]-propan-1-ol

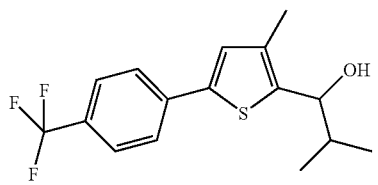

Preparation 29

1-[3-Methyl-5-(4-trifluoromethyl-phenyl)-thiophen-2-yl]-2-phenyl-ethanol

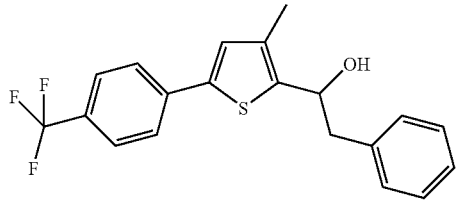

Preparation 30

[3-Isopropyl-5-(4-trifluoromethyl-phenyl)-thiophen-2-yl]-methanol

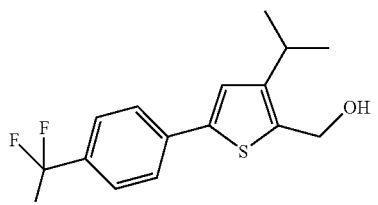

Step A

2-Formyl-5-(4-trifluoromethyl-phenyl)-thiophene-3-boronic acid

The titled compound is prepared from 5-(4-Trifluoromethyl-phenyl)-thiophene-2-carbaldehyde (2.70 g, 10 mmole) and trimethyl borate (5.68 g, 50.0 mmole) in a similar manner to 3-Methyl-5-(4-trifluoromethyl-phenyl)-thiophene-2-carbaldehyde.

Step B

3-Isopropenyl-5-(4-trifluoromethyl-phenyl)-thiophene-2-carbaldehyde

To a mixture of 2-Formyl-5-(4-trifluoromethyl-phenyl)-thiophene-3-boronic acid (0.330 g, 1.10 mmole), 2-Bromopropene (0.399 g, 3.30 mmole) and cesium fluoride (0.585 g, 3.85 mmole) in dioxane (5 mL), is bubbled with nitrogen gas for 15 minutes. The catalyst $PdCl_2$ (dppf) (0.033 g) is then added to the mixture. The reaction is heated under reflux for 16 hours. The solvent is removed on rota vapor, and the resulting residue is partitioned between ethyl acetate (20 ml) and water (20 mL). The aqueous layer is extracted with more ethyl acetate (20 mL). The combined organic solution is washed with brine (3×50 mL), dried over $Na_2SO_4$ and concentrated. The crude product is purified on a silica gel column, eluting with 0-15% ethyl acetate in hexane and concentrated to provide the titled compound as pale yellow crystalline.

Step C

[3-Isopropenyl-5-(4-trifluoromethyl-phenyl)-thiophen-2-yl]-methanol

To a solution of 3-Isopropenyl-5-(4-trifluoromethyl-phenyl)-thiophene-2-carbaldehyde (0.084 g, 0.283 mmole) in THF (3 mL), is added to $NaBH_4$ (0.023 g, 0.622 mmole) in one portion at 0° C. The reaction is kept at 0° C. for 15 minutes and warmed up to room temperature for 2 hours. The reaction is quenched using saturated $NH_4Cl_{(aq)}$ (20 mL) at 0° C. The THF is removed on rota vapor, the aqueous solution is then extracted with ethyl acetate (2×10 mL). The combined organic solution is washed with brine (3×20 mL), dried over $Na_2SO_4$ and concentrated to provide the titled compound as yellow solid, which is used for the next step without further purification.

Step D

[3-Isopropyl-5-(4-trifluoromethyl-phenyl)-thiophen-2-yl]-methanol

The solution of [3-Isopropenyl-5-(4-trifluoromethyl-phenyl)-thiophen-2-yl]-methanol (0.084 g, 0.282 mmole) is stirred under nitrogen gas in presence of 10% palladium on carbon (0.085 g) for 16 hours. The catalyst is removed by filtration, and the filtrate is concentrated to provide the titled compound as white solid, which is used for the next step without further purification.

Preparation 31

2-[3-Methyl-5-(4-trifluoromethyl-phenyl)-thiophen-2-yl]-propan-1-ol

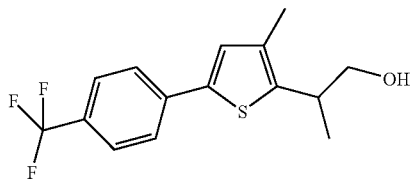

Step A

1-[3-Methyl-5-(4-trifluoromethyl-phenyl)-thiophen-2-yl]-ethanone

To a solution of 1-[3-Methyl-5-(4-trifluoromethyl-phenyl)-thiophen-2-yl]-ethanol (see Preparation 8) (4.40 g, 15.4 mmole), is added $MnO_2$ (7.88 g, 77.0 mmole) in one portion. The mixture is heated under reflux for 16 hours, more $MnO_2$ (7.88 g, 77.0 mmole) is added to the reaction and continued to reflux for 4 hours. The mixture is filtered through a celite pad, and the mother liquid is concentrated. The crude product is purified on a silica gel column, gradient eluting with 0-20% ethyl acetate in hexane and concentrated to provide the titled compound as yellow solid.

Step B

2-[3-Methyl-5-(4-trifluoromethyl-phenyl)-thiophen-2-yl]-propionaldehyde

To a solution of (methoxymethyl)triphenyl phosphonium chloride (3.96 g, 10.76 mmole) in toluene/THF (2:1, 60 mL), is added potassium t-butoxide (1.21 g, 10.76 mmole) in one portion and stirred for 30 minutes. To the resulting ylide, is injected into a solution of 1-[3-Methyl-5-(4-trifluoromethyl-phenyl)-thiophen-2-yl]-ethanone (1.53 g, 5.38 mmole). The reaction is stirred for 2 hours, and then concentrated on rota vapor. The residue is purified on a silica gel column, eluting with 0-10% ethyl acetate in hexane and concentrated to provide 2-(2-Methoxy-1-methyl-vinyl)-3-methyl-5-(4-trifluoromethyl-phenyl)-thiophene as brown oil. The generated vinyl ether is treated with concentrated $HCl_{(aq)}$ (2 mL) in THF (60 mL) at 60° C. for 2 hours. The solvents are removed on rota vapor, and the residue is purified on a silica gel column, eluting with 0-20% ethyl acetate in hexane and concentrated to provide the titled compound as colorless oil.

Step C

2-[3-Methyl-5-(4-trifluoromethyl-phenyl)-thiophen-2-yl]-propan-1-ol

To a solution of 2-[3-Methyl-5-(4-trifluoromethyl-phenyl)-thiophen-2-yl]-propionaldehyde (1.40 g, 4.69 mmole) in THF (20 mL), is added to $NaBH_4$ (0.266 g, 7.04 mmole) in one portion at 0° C. The reaction is kept at 0° C. for 15 minutes and warmed up to room temperature for 2 hours. The reaction is quenched using $NH_4Cl_{(aq)}$ (50 mL) at 0° C. The THF is removed on rota vapor, the aqueous solution is then extracted with ethyl acetate (2×50 mL). The combined organic solution is washed with brine (3×100 mL), dried over $Na_2SO_4$ and concentrated. The crude product is purified on a silica gel column, gradient eluting with 0-20% ethyl acetate in hexane and concentrated to provide the titled compound as white solid.

The racemic material is resolved on a Chiralpak AD column (4.6×250 mm). Eluted with 100% methanol and concentrated the fractions of the faster component to provide pure enantiomer (isomer 1, 100% ee) and slower component to provide another enantiomer (isomer II, >99.5% ee).

Preparation 32

1-(2-Methyl-5-phenyl-thiophen-3-yl)-ethanol

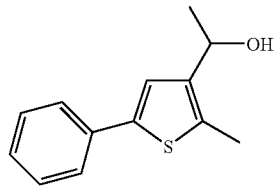

To a solution of 1-(2-Methyl-5-phenyl-thiophen-3-yl)-ethanone (1.08 g, 5.00 mmole) in THF (20 mL), is added to LiBH$_4$ (0.327 g, 15.0 mmole) in one portion at 0° C. The reaction is kept at 0° C. for 30 minutes and warmed up to room temperature for 2 hours. The reaction is quenched using NH$_4$Cl$_{(aq)}$ (50 mL) at 0° C. The THF is removed on rota vapor, the aqueous solution is then extracted with ethyl acetate (3×50 mL). The combined organic solution is dried over Na$_2$SO$_4$ and concentrated to provide the titled compound as white solid, which is used for the next step without further purification.

Preparation 33

1-[3-Methyl-5-(4-trifluoromethyl-phenyl)-thiophen-2-yl]-ethanol

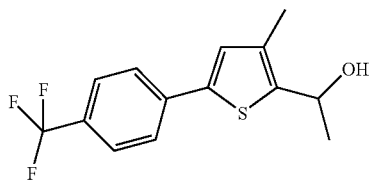

To a solution of 3-methyl-5-(4-Trifluoromethyl-phenyl)-thiophene-2-carbaldehyde (0.130 g, 0.481 mmole) in THF (5 mL), is injected 3.0 M MeMgBr in ethyl ether (0.27 mL, 0.810 mmole) dropwise. The reaction is stirred for 2 hours. The reaction is quenched with saturated NH$_4$Cl$_{(aq)}$ (10 mL), then the aqueous solution is extracted with ethyl acetate (3×15 mL). The combined organic solution is washed with brine (3×50 mL), dried over Na$_2$SO$_4$ and concentrated. The crude product is purified on a silica gel column, eluting with 0-20% ethyl acetate in hexane and concentrated to provide the titled compound as yellow solid.

The following compounds (Preparation 34 to 39) are made in a similar manner:

Preparation 34

[3-Iodo-5-4-trifluoromethyl-phenyl)-thiophen-2-yl]-methanol

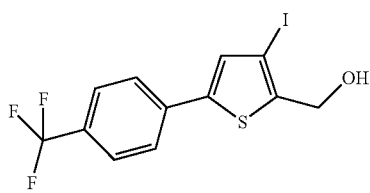

Preparation 35

1-[3-Iodo-5-(4-trifluoromethyl-phenyl)-thiophen-2-yl]-ethanol

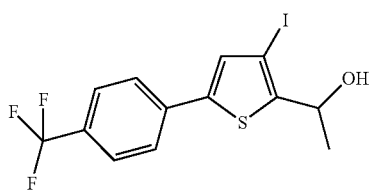

Preparation 36

1-[3-Methyl-5-(4-trifluoromethyl-phenyl)-thiophen-2-yl]-propan-1-ol

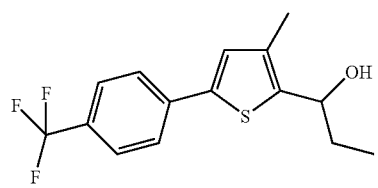

Preparation 37

1-[3-Methyl-5-(4-trifluoromethyl-phenyl)-thiophen-2-yl]-butan-1-ol

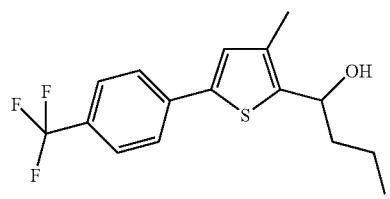

Preparation 38

2-Methyl-1-[3-methyl-5-(4-trifluoromethyl-phenyl)-thiophen-2-yl]-propan-1-ol

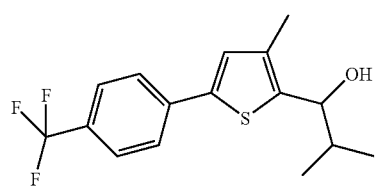

Preparation 39

1-[3-Methyl-5-(4-trifluoromethyl-phenyl)-thiophen-2-yl]-2-phenyl-ethanol

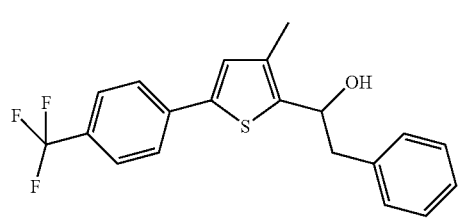

Preparation 40

[3-Isopropyl-5-(4-trifluoromethyl-phenyl)-thiophen-2-yl]-methanol

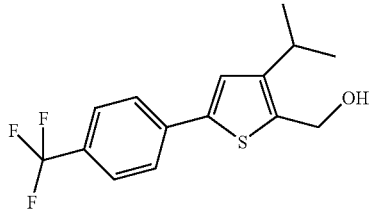

Step A

2-Formyl-5-(4-trifluoromethyl-phenyl)-thiophene-3-boronic acid

The titled compound is prepared from 5-(4-Trifluoromethyl-phenyl)-thiophene-2-carbaldehyde (2.70 g, 10 mmole) and trimethyl borate (5.68 g, 50.0 mmole) in a similar manner to 3-Methyl-5-(4-trifluoromethyl-phenyl)-thiophene-2-carbaldehyde (Preparation 2, Step A).

Step B

3-Isopropenyl-5-(4-trifluoromethyl-phenyl)-thiophene-2-carbaldehyde

To a mixture of 2-Formyl-5-(4-trifluoromethyl-phenyl)-thiophene-3-boronic acid (0.330 g, 1.10 mmole), 2-Bromopropene (0.399 g, 3.30 mmole) and cesium fluoride (0.585 g, 3.85 mmole) in dioxane (5 mL), is bubbled with nitrogen gas for 15 minutes. The catalyst $PdCl_2$ (dppf) (0.033 g) is then added to the mixture. The reaction is heated under reflux for 16 hours. The solvent is removed on rota vapor, and the resulting residue is partitioned between ethyl acetate (20 ml) and water (20 mL). The aqueous layer is extracted with more ethyl acetate (20 mL). The combined organic solution is washed with brine (3×50 mL), dried over $Na_2SO_4$ and concentrated. The crude product is purified on a silica gel column, eluting with 0-15% ethyl acetate in hexane and concentrated to provide the titled compound as pale yellow crystalline.

Step C

[3-Isopropenyl-5-(4-trifluoromethyl-phenyl)-thiophen-2-yl]-methanol

To a solution of 3-Isopropenyl-5-(4-trifluoromethyl-phenyl)-thiophene-2-carbaldehyde (0.084 g, 0.283 mmole) in THF (3 mL), is added to $NaBH_4$ (0.023 g, 0.622 mmole) in one portion at 0° C. The reaction is kept at 0° C. for 15 minutes and warmed up to room temperature for 2 hours. The reaction is quenched using saturated $NH_4Cl_{(aq)}$ (20 mL) at 0° C. The THF is removed on rota vapor, the aqueous solution is then extracted with ethyl acetate (2×10 mL). The combined organic solution is washed with brine (3×20 mL), dried over $Na_2SO_4$ and concentrated to provide the titled compound as yellow solid, which is used for the next step without further purification.

Step D

[3-Isopropyl-5-(4-trifluoromethyl-phenyl)-thiophen-2-yl]-methanol

The solution of [3-Isopropenyl-5-(4-trifluoromethyl-phenyl)-thiophen-2-yl]-methanol (0.084 g, 0.282 mmole) is stirred under nitrogen gas in presence of 10% palladium on carbon (0.085 g) for 16 hours. The catalyst is removed by filtration, and the filtrate is concentrated to provide the titled compound as white solid, which is used for the next step without further purification.

Preparation 41

2-[3-Methyl-5-4-trifluoromethyl-phenyl)-thiophen-2-yl]-propan-1-ol

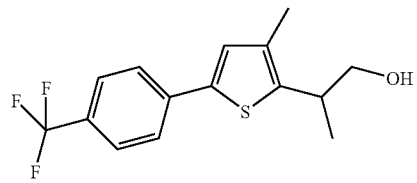

Step A

1-[3-Methyl-5-(4-trifluoromethyl-phenyl)-thiophen-2-yl]-ethanone

To a solution of 1-[3-Methyl-5-(4-trifluoromethyl-phenyl)-thiophen-2-yl]-ethanol (see Preparation 2)(4.40 g, 15.4 mmole), is added $MnO_2$ (7.88 g, 77.0 mmole) in one portion. The mixture is heated under reflux for 16 hours, more $MnO_2$ (7.88 g, 77.0 mmole) is added to the reaction and continued to reflux for 4 hours. The mixture is filtered through a celite pad, and the mother liquid is concentrated. The crude product is purified on a silica gel column, gradient eluting with 0-20% ethyl acetate in hexane and concentrated to provide the titled compound as yellow solid.

Step B

2-[3-Methyl-5-(4-trifluoromethyl-phenyl)-thiophen-2-yl]-propionaldehyde

To a solution of (methoxymethyl)triphenyl phosphonium chloride (3.96 g, 10.76 mmole) in toluene/THF (2:1, 60 mL), is added potassium t-butoxide (1.21 g, 10.76 mmole) in one portion and stirred for 30 minutes. To the resulting ylide, is injected into a solution of 1-[3-Methyl-5-(4-trifluoromethyl-phenyl)-thiophen-2-yl]-ethanone (1.53 g, 5.38 mmole). The reaction is stirred for 2 hours, and then concentrated on rota vapor. The residue is purified on a silica gel column, eluting with 0-10% ethyl acetate in hexane and concentrated to provide 2-(2-Methoxy-1-methyl-vinyl)-3-methyl-5-(4-trifluoromethyl-phenyl)-thiophene as brown oil. The generated vinyl ether is treated with concentrated $HCl_{(aq)}$ (2 mL) in THF(60 mL) at 60° C. for 2 hours. The solvents are removed on rota vapor, and the residue is purified on a silica gel column, eluting with 0-20% ethyl acetate in hexane and concentrated to provide the titled compound as colorless oil.

Step C

2-[3-Methyl-5-(4-trifluoromethyl-phenyl)-thiophen-2-yl]-propan-1-ol

To a solution of 2-[3-Methyl-5-(4-trifluoromethyl-phenyl)-thiophen-2-yl]-propionaldehyde (1.40 g, 4.69 mmole) in THF (20 mL), is added to NaBH$_4$ (0.266 g, 7.04 mmole) in one portion at 0° C. The reaction is kept at 0° C. for 15 minutes and warmed up to room temperature for 2 hours. The reaction is quenched using NH$_4$Cl$_{(aq)}$ (50 mL) at 0° C. The THF is removed on rota vapor, the aqueous solution is then extracted with ethyl acetate (2×50 mL). The combined organic solution is washed with brine (3×100 mL), dried over Na$_2$SO$_4$ and concentrated. The crude product is purified on a silica gel column, gradient eluting with 0-20% ethyl acetate in hexane and concentrated to provide the titled compound as white solid.

The racemic material is resolved on a Chiralpak AD column (4.6×250 mm). Eluted with 100% methanol and concentrated the fractions of the faster component to provide pure enantiomer (isomer 1, 100% ee) and slower component to provide another enantiomer (isomer II, >99.5% ee).

Preparation 42

1-(2-Methyl-5-phenyl-thiophen-3-yl)-ethanol

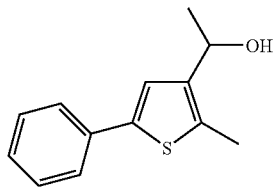

To a solution of 1-(2-Methyl-5-phenyl-thiophen-3-yl)-ethanone (1.08 g, 5.0.0 mmole) in THF (20 mL), is added to LiBH$_4$ (0.327 g, 15.0 mmole) in one portion at 0° C. The reaction is kept at 0° C. for 30 minutes and warmed up to room temperature for 2 hours. The reaction is quenched using NH$_4$Cl$_{(aq)}$ (50 mL) at 0° C. The THF is removed on rota vapor, the aqueous solution is then extracted with ethyl acetate (3×50 mL). The combined organic solution is dried over Na$_2$SO$_4$ and concentrated to provide the titled compound as white solid, which is used for the next step without further purification.

EXAMPLE 1

3-{2-Methyl-4-[5-4-trifluoromethyl-phenyl)-thiophen-2-ylmethoxy]-phenyl}-propionic acid

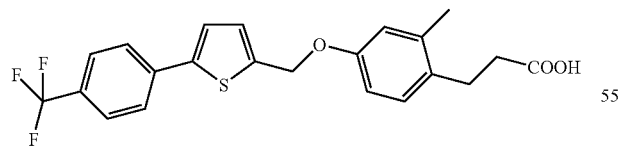

Step A

3-{2-Methyl-4-[5-(4-trifluoromethyl-phenyl)-thiophen-2-ylmethoxy]-phenyl}-propionic acid methyl ester To a solution of 2-Chloromethyl-5-(4-trifluoromethyl-phenyl)-thiophene (0.210 g, 0.760 mmole) and 3-(4-Hydroxy-2-methyl-phenyl)-propionic acid methyl ester (0.147 g, 0.760 mmole) in acetonitrile (5 mL), is added cesium carbonate (0.248 mL, 0.760 mmole) in one portion. The reaction is heated at 50° C. overnight, then concentrated. The residue is loaded to a silica gel column, eluted with ethyl acetate in hexane (0-15%) and concentrated to provide the titled compound as a white solid.

Step B

3-{2-Methyl-4-[5-(4-trifluoromethyl-phenyl)-thiophen-2-ylmethoxy]-phenyl}-propionic acid 3-{2-Methyl-4-[5-(4-trifluoromethyl-phenyl)-thiophen-2-ylmethoxy]-phenyl}-propionic acid methyl ester (0.170 g, 0.390 mmole) is treated with a mixture of NaOH$_{(aq)}$ (1 mL)/THF (3 mL)/MeOH (3 mL) at room temperature overnight. The organic solvents are removed on rota-vapor. The residue is diluted with water (10 mL), acidified to pH=2 with 6N HCl$_{(aq)}$. The precipitate is collected through filtration, washed with cold water (30 mL) and dried to provide the titled compound as white solid. MS (ES):419 (M+H)⁻, the structure is also confirmed by proton NMR.

The following compound (Example 2) is made in a similar manner:

EXAMPLE 2

{2-Methyl-4-[5-(4-trifluoromethyl-phenyl)-thiophen-2-ylmethoxy]-phenoxy}-acetic acid

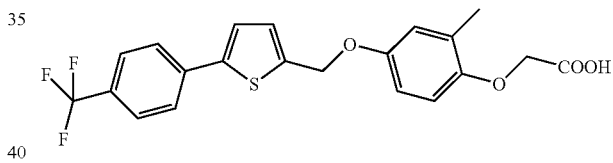

MS (ES): 421 (M+H)⁻, the structure is also confirmed by proton NMR.

Synthesis Method for Examples 3-8

Examples 3 through 8 are made substantially as described:

Step A

3-{2-Methyl-4-[5-(4-trifluoromethyl-phenyl)-thiophen-2-ylmethoxy]-phenyl}-propionic acid methyl ester To a solution of [5-(4-Trifluoromethyl-phenyl)-thiophen-2-yl]-methanol (0.063 g, 0.232 mmole) and 3-(4-Hydroxy-2-methyl-phenyl)-propionic acid methyl ester (0.045 g, 0.232 mmole) in toluene (2 mL) at room temperature, is added tributylphosphine (0.087 mL, 0.348 mmole) followed by a solution of 1,1'-(azodicarbonyl)-dipiperidine (0.088 g, 0.348 mmole) in toluene (2 mL). The reaction is stirred overnight, and then diluted with hexane (10 mL). The precipitate is removed through filtration and the filtrate is concentrated, loaded to a silica gel column, eluted with ethyl acetate in hexane (0-15%) and concentrated to provide the titled compound as white solid.

Step B

3-{2-Methyl-4-[3-methyl-5-(4-trifluoromethyl-phenyl)-thiophen-2-ylmethoxy]-phenyl}-propionic acid 3-{2-Methyl-4-[5-(4-trifluoromethyl-phenyl)-thiophen-2-ylmethoxy]-phenyl}-propionic acid methyl ester (0.043 g, 0.0959 mmole) is treated with a mixture of NaOH $_{(aq)}$ (1 mL)/THF (3 mL)/MeOH (3 mL) at room temperature overnight. The organic solvents are removed on rota-vapor. The residue is diluted with water (10 mL), acidified to pH=2 with 6N HCl$_{(aq)}$. The precipitate is collected through filtration, washed with cold water (30 mL) and dried to provide the titled compound as a white solid. MS (ES): 433 (M+H)⁻, the structure is also confirmed by proton NMR.

EXAMPLE 3

3-{2-Methyl-4-[3-phenyl-5-(4-trifluoromethyl-phenyl)-thiophen-2-ylmethoxy]-phenyl}-propionic acid

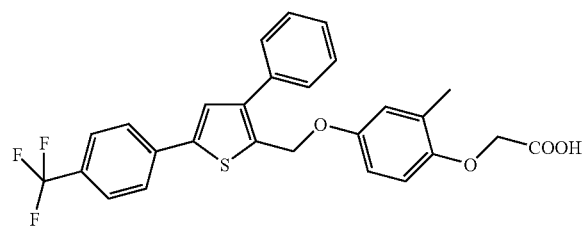

MS (ES): 495 (M+H)⁻, the structure is also confirmed by proton NMR.

EXAMPLE 4

3-{4-[3,5-Bis-(4-trifluoromethyl-phenyl)-thiophen-2-ylmethoxy]-2-methyl-phenyl}-propionic acid

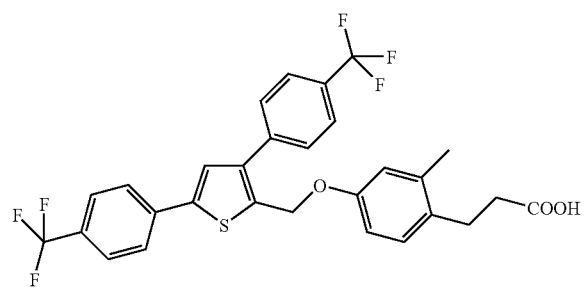

MS (ES): 563 (M+H)⁻, the structure is also confirmed by proton NMR.

EXAMPLE 5

3-(2-Methyl-4-{1-[3-methyl-5-(4-trifluoromethyl-phenyl)-thiophen-2-yl]-propoxy}-phenyl)-propionic acid

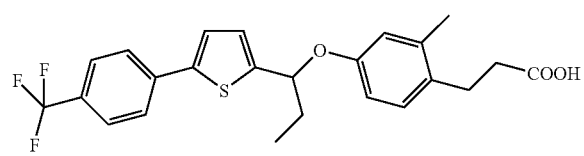

MS (ES): 447 (M+H)⁻, the structure is also confirmed by proton NMR.

EXAMPLE 6

3-(2-Methyl-4-{1-[3-methyl-5-(4-trifluoromethyl-phenyl)-thiophen-2-yl]-butoxy}-phenyl)-propionic acid

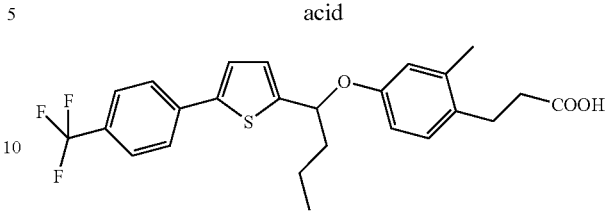

MS (ES): 461 (M+H)⁻, the structure is also confirmed by proton NMR.

EXAMPLE 7

3-(2-Methyl-4-{2-methyl-1-[3-methyl-5-(4-trifluoromethyl-phenyl)-thiophen-2-yl]-propoxy}-phenyl)-propionic acid

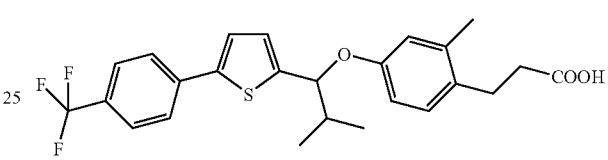

MS (ES): 461 (M+H)⁻, the structure is also confirmed by proton NMR.

EXAMPLE 8

3-(2-Methyl-4-{1-[3-methyl-5-(4-trifluoromethyl-phenyl)-thiophen-2-yl]-2-phenyl-ethoxy}-phenyl)-propionic acid

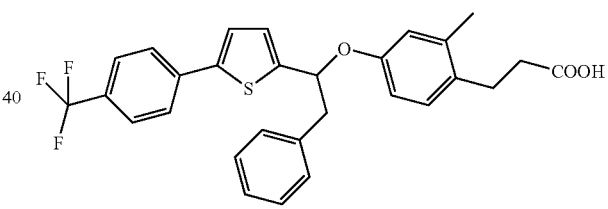

MS (ES): 509 (M+H)⁻, the structure is also confirmed by proton NMR.

Synthesis Method for Example 9

Step A 3-(4-{1-[3-Iodo-5-(4-trifluoromethyl-phenyl)-thiophen-2-yl]-ethylsulfanyl}-2-methyl-phenyl)-propionic acid methyl ester To a solution of 1-[3-Iodo-5-(4-trifluoromethyl-phenyl)-thiophen-2-yl]-ethanol (1.52 g, 3.96 mmole) and 3-(4-Mercapto-2-methyl-phenyl)-propionic acid methyl ester (0.769 g, 3.96 mmole) in toluene (20 mL) at room temperature, is added tributylphosphine (1.98 mL, 7.92 mmole) followed by a solution of 1,1'-(azodicarbonyl)-dipiperidine (1.99 g, 7.92 mmole) in toluene (20 mL). The reaction is stirred overnight, and then diluted with hexane (100 mL). The precipitate is removed through filtration and the filtrate is concentrated, loaded to a silica gel column, eluted with ethyl acetate in hexane (0-15%) and concentrated to provide the titled compound as yellow solid.

Step B

3-(2-Methyl-4-{1-[5-(4-trifluoromethyl-phenyl)-3-vinyl-thiophen-2-yl]-ethylsulfanyl}-phenyl)-propionic acid methyl ester The solution of 3-(4-{1-[3-Iodo-5-(4-trifluoromethyl-phenyl)-thiophen-2-yl]-ethylsulfanyl}-2-methyl-phenyl)-propionic acid methyl ester (0.195 g, 0.348 mmole) and tributyl(vinyl)tin (0.331 g, 1.04 mmole) in toluene (3 mL) is bubbled with nitrogen gas for 10 minutes. To it is added tetrakis(triphenylphosphine)palladium(0) (0.20 g). The reaction is heated under 80° C. overnight. The mixture is concentrated, loaded to a silica gel column, eluted with ethyl acetate in hexane (0-15%) and concentrated to provide the titled compound as colorless oil.

Step C

3-(4-{1-[3-(2-Hydroxy-ethyl)-5-(4-trifluoramethyl-phenyl)-thiophen-2-yl]-ethylsulfanyl}-2-methyl-phenyl)-propionic acid To a solution of 3-(2-Methyl-4-{1-[5-(4-trifluoromethyl-phenyl)-3-vinyl-thiophen-2-yl]-ethylsulfanyl}-phenyl)-propionic acid methyl ester (0.365 g, 0.744 mmole) in THF (5 mL) at 0° C., is added dropwise 1.0N $BH_3$/THF complex (3.0 mL, 3.0 mmole). The mixture is warmed up to room temperature and stirred for an hour. To it is added 30% $H_2O_2$ (10 mL) and 1.0 N $NaOH_{(aq)}$ (10 mL), and the reaction is heated under reflux for 2 hours. It is then acidified by adding concentrated HCl carefully to pH=2. The aqueous solution is extracted with ethyl acetate (3×20 mL), and the combine organic solution is dried and concentrated. The crude product is purified by reverse phase preparative HPLC, eluting with 5.0 nM $NH_4HCO_{3(aq)}$/$CH_3CN$ and concentration of fractions to provide the titled compound as a white solid.

EXAMPLE 9

3-(4-{1-[3-(2-Hydroxy-ethyl)-5-(4-trifluoromethyl-phenyl)-thiophen-2-yl]-ethylsulfanyl}-2-methyl-phenyl)-propionic acid

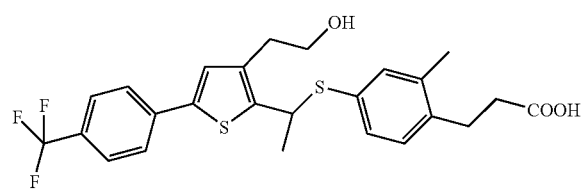

MS (ES): 493 (M+H)$^-$, the structure is also confirmed by proton NMR.

EXAMPLE 10 (Isomer II)

2-Methoxy-3-(4-{2-[3-methyl-5-(4-trifluoromethyl-phenyl)-thiophen-2-yl]-propoxy}-phenyl)-propionic acid

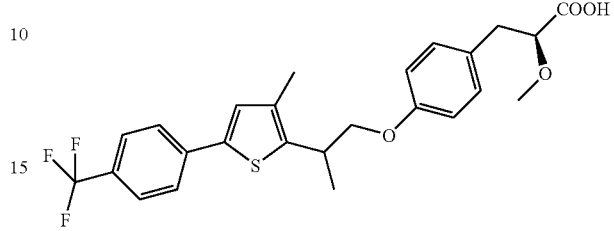

MS (ES): 479 (M+H)$^+$, 477 (M+H)$^-$, the structure is also confirmed by proton NMR.

EXAMPLE 11 (Isomer II)

2-Methyl-3-(4-{2-[3-methyl-5-(4-trifluoromethyl-phenyl)-thiophen-2-yl]-propoxy}-phenyl)-2-phenoxy-propionic acid

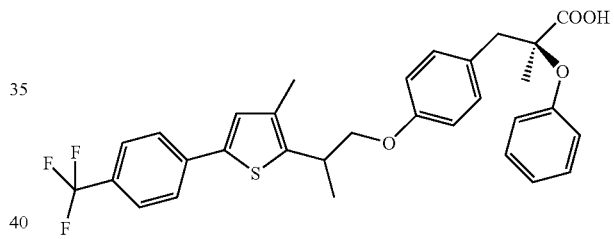

MS (ES): 572 (M+NH$_4$)$^+$, 553 (M+H)$^-$, the structure is also confirmed by proton NMR.

EXAMPLE 12 (Isomer I)

(2-Methyl-4-{2-[3-methyl-5-(4-trifluoromethyl-phenyl)-thiophen-2-yl]-propylsulfanyl}-phenoxy)-acetic acid

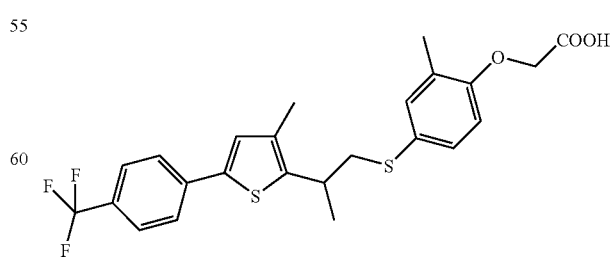

MS (ES): 481 (M+H)$^+$, 479 (M–H)$^-$, the structure is also confirmed by proton NMR.

EXAMPLE 13 (Isomer II)

(2-Methyl-4-{2-[3-methyl-5-(4-trifluoromethyl-phenyl)-thiophen-2-yl]-propylsulfanyl}-phenoxy)-acetic acid

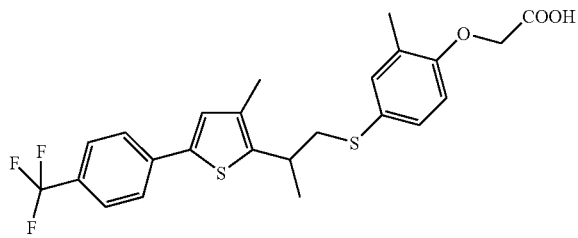

MS (ES): 481 (M+H)$^+$, 479 (M−H)$^−$, the structure is also confirmed by proton NMR.

EXAMPLE 14 (Isomer II)

3-(2-Methyl-4-{2-[3-methyl-5-(4-trifluoromethyl-phenyl)-thiophen-2-yl]-propylsulfanyl}-phenyl)-propionic acid

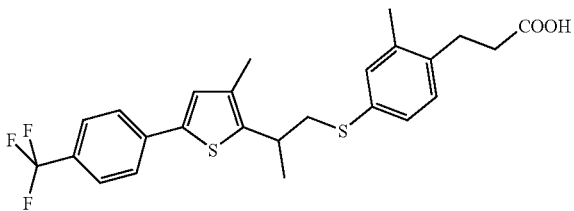

MS (ES) 479 (M+H)$^+$, 477 (M−H)$^−$, the structure is also confirmed by proton NMR.

EXAMPLE 15 (Isomer II)

(3-{2-[3-Methyl-5-(4-trifluoromethyl-phenyl)-thiophen-2-yl]-propoxy}-phenyl)-acetic acid

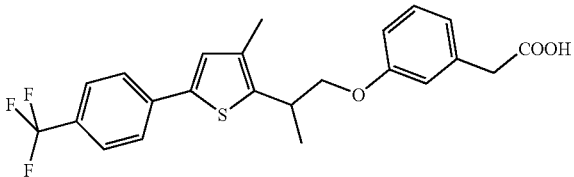

MS (ES): 435 (M+H)$^+$, 433 (M−H)$^−$, the structure is also confirmed by proton NMR.

EXAMPLE 16

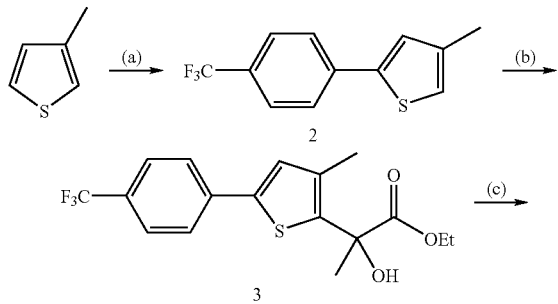

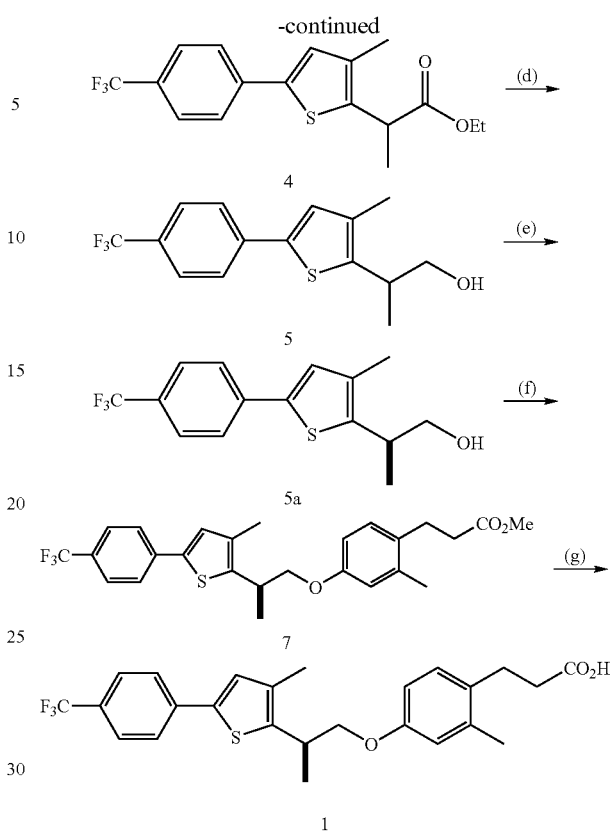

Conditions: (a) BuLi, B(OMe)$_3$, THF, then H$_2$O, Na$_2$CO$_3$, Pd(OAc)$_2$, PPh$_3$, 4-I—C$_4$H$_4$—CF$_3$, 65%; (b) BuLi, THF, −65° C., CH$_3$C(O)CO$_2$Et; (c) Et$_3$SiH, TFA, CH$_2$Cl$_2$, 0° C.; (d) LAH, THF, 0° C., 78% over (b), (c) and (d); (e) ) Chiralpak AD 4.6 × 250 mm, methanol, 1 mL/min, 47%; (f) 6, PBu$_3$, ADDP, toluene, rt, 3 h, 79.5%; (g) NaOH, THF/MeOH, rt, 1 h, crystallize, 88%.

The newly developed three-step sequence from 2 to 5, affords 5 in an overall 78% yield (avg. 92% per step).

The final saponification and crystallization proceed without incident.

Compound 1 is obtained in an overall yield of 17%.

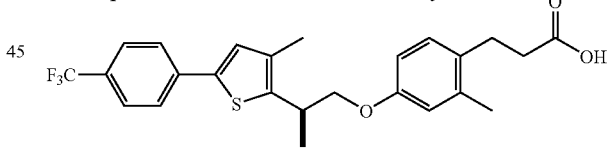

3-(2-Methyl-4-{2-[3-methyl-5-(4-trifluoromethylphenyl)thiophen-2-yl]propoxy}-phenyl)propionic acid (isomer 2) (1)$^1$ 3-(2-Methyl-4-{2-[3-methyl-5-(4-trifluoromethylphenyl)thiophen-2-yl]propoxy}phenyl)propionic acid methyl ester (isomer 2, 398 g, 0.84 mol) is dissolved in THF and MeOH (3800 mL). To the resulting clear yellow solution is added aq. NaOH (335 mL, 1.68 mol) over 15 minutes. The solution is stirred at rt for 2 h, then transferred to rotary evaporator and concentrated in vacuo at 40° C. to a pale yellow paste. This paste is partitioned between 1N aq. HCl (1700 mL, 1.7 mol) and EtOAc (2000 mL). The aq. layer is back-extracted with EtOAc (2000 mL) and the combined organic layers are washed with sat'd aq. NaCl (2000 mL), dried (Na$_2$SO$_4$), filtered and concentrated to a pale yellow solid. This solid is recrystallized from a mixture of EtOAc (1000 mL) and n-heptane (3000 mL), cooled to 0° C. and filtered. The solids are rinsed with cold hexanes (1000 mL). The product is dried in vacuo at 45° C. to afford the title compound as a white crystalline solid (338 g, 88%). mp: 126.2-132.6° C. $^1$H NMR (CDCl$_3$) δ (dd, 4H, J=25, 8 Hz), 7.14 (s, 1H), 7.07 (d, 1H, J=8 Hz), 6.76 (s, 1H), 6.72 (d, 1H, J=8 Hz), 4.08 (t, 1H, J=6 Hz), 3.69 (t, 1H, J=7 Hz), 3.61 (m, 1H), 2.91 (t, 2H, J=8 Hz), 2.64 (t, 2H, J=8 Hz), 2.31 (s, 3H), 2.27 (s, 3H), 1.49 (d, 3H, J=8 Hz); $^{13}$C NMR (CDCl$_3$) δ 179.7, 157.5, 142.5, 138.6, 138.2, 137.6, 134.9, 130.9, 129.7, 128.9 (q, J=33 Hz), 127.6, 126.0, 125.6, 123.4, 116.9, 112.1, 73.2, 34.9, 34.0, 27.5, 19.7, 19.5, 14.2; IR (CHCl$_3$) 2963, 2923, 1713, 1614, 1502, 1329, 1194, 1120, 1070, 823 cm$^{-1}$; Anal. Calcd. for C$_{25}$H$_{25}$F$_3$O$_3$S: C, 64.92; H, 5.45; F, 12.32; S, 6.93. Found: C, 64.95; H, 5.49; F, 12.05; S, 6.95.

BIOLOGICAL ASSAYS

Binding and Cotransfection Studies

The in vitro potency of compounds in modulating PPARα receptors are determined by the procedures detailed below. DNA-dependent binding (ABCD binding) is carried out using SPA technology with PPAR receptors. Tritium-labeled PPARα agonists are used as radioligands for generating displacement curves and IC$_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 μM).

These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα.

The binding and cotransfection efficacy values for compounds of the invention which are especially useful for modulating a PPAR receptor, are ≦100 nM and ≧50%, respectively.

Evaluation of Triglyceride Reduction and HDL Cholesterol Elevation in HuapoAI Transgenic Mice Compounds of the present invention are studied for effects upon HDL and triglyceride levels in human apoAI mice. For each compound tested, seven to eight week old male mice, transgenic for human apoAI (C57BL/6-tgn(apoa1)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO2 and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured calorimetrically using commercially prepared reagents (for example, as available from Sigma #339-1000 and Roche #450061 for triglycerides and cholesterol, respectively). The procedures are modified from published work (McGowan M. W. et al., Clin Chem 29:538-542,1983; Allain C. C. et al., Clin Chem 20:470-475,1974. Commercially available standards for triglycerides and total cholesterol, respectively, commercial quality control plasma, and samples are measured in duplicate using 200 μl of reagent. An additional aliquot of sample, added to a well containing 200 μl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow strem at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL). is calculated using Perkin Elmer Turbochrome software.

Triglyceride Serum Levels in Mice Dosed with a Compound of the Invention is Compared to Mice Receiving the Vehicle to identify compounds which could be particularly useful for flowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects upon plasma glucose associated with administering various dose levels of different compounds of the present invention and the PPAR gamma agonist rosiglitazone (BRL49653) or the PPAR alpha agonist fenofibrate, and the control, to male db/db mice, are studied.

Five week old male diabetic (db/db) mice [for example, C57BlKs/j-m+/+Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 μl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween 80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24-hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific colorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 μl/well) are measured in duplicate using 200 μl of reagent. An additional aliquot of sample, pipetted to a third well and diluted in 200 μl water, provided a blank for each specimen. Plates are incubated at room temperature for 18 minutes for glucose on a plate shaker (DPC Micormix 5) and absorbance read at 500 nm on a plate reader. Sample absorbances are compared to a standard-curve (100-800 for glucose). Values for the quality control sample are always within the expected range and the coefficient of variation for samples is below 10%. All samples from an experiment are assayed at the same time to minimize inter-assay variability.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealing a significant reduction in respiratory quotient (RQ) in treated animals during the dark cycle [0.864±0.013 (Control) vs. 0.803±0.007 (Treated); p<0.001] is indicative of an increased utilization of fat during the animals' active (dark) cycle and can be used to selected especially desired compounds of this invention. Additionally, treated animals displaying significantly higher rates of energy expenditure than control animals suggest such compounds of this invention can be especially desired.

Male $KK/A^y$ Mice

Male $KK/A^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention which may be especially desired.

Method to Elucidate the LDL-Cholesterol Total-Cholesterol and Triglyceride Lowering Effect Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180-280 mg/dl. (Hamsters fed with normal chow have a total plasma cholesterol level between 100-150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster received once a day approx. 1 ml of the solution by garvage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's precedure. Plasma lipoproteins (VLDL, LDL and HDL) are resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. Especially desired compounds are markedly more potent than fenofibrate in LDL-lowering efficacy. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired. The known control fenofibrate did not show significant efficacy under the same experimental conditions.

Method to Elucidate the Fibrinogen-Lowering Effect of PPAR Modulators

Zucker Fatty Rat Model:

The life phase of the study on fibrinogen-lowering effect of compounds of this invention is part of the life phase procedures for the antidiabetic studies of the same compounds. On the last ($14^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a ½₀ dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples. Compounds that lower fibrinogen level greater than vehicle can be especially desired.

Cholesterol and triglyceride lowering effects of compounds of this invention are also studied in Zucker rats.

Method to Elucidate the Anti-Body Weight Gain and Anti-Appetite Effects of Compounds of this Invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Compounds of this invention are dissolved in an aqueous vehicle such that each rat received once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored.

Using this assay, compounds of this invention are identified to determine which can be associated with significant weight reduction.

Method to Elucidate the Activation of the PPAR Delta Receptor in Vivo

This method is particularly useful for measuring the in vivo PPARdelta receptor activation of compounds of this invention that are determined to possess significant in vitro activity for that receptor isoform over the PPAR gamma isoform.

Male PPARa null mice (129s4 SvJae-PPARa<tm1Gonz> mice; Jackson Laboratories) of 8-9 weeks of age are maintained on Purina 5001 chow with water ad libitum for at least one week prior to use. Feed and water are provided ad libitum throughout the course of the experiment. Using the GroupOptimizeV211.xls program, mice are randomized into treatment groups of five animals each based on their body weight.

Compounds of this invention are suspended in an aqueous vehicle of 1% (w/v) carboxymethylcellulose and 0.25% Tween 80 such that each mouse receives once a day approx. 0.2 ml of the solution by gavage at doses ranging from 0.2 to 20 mg/kg body weight. A control group of mice is included in each experiment whereby they are dosed in parallel with vehicle alone. Dosing is performed daily in the early morning for 7 days.

On the last day of dosing, mice are euthanized by CO2 asphyxiation 3 hours after the final dose. Blood samples are collected by heart draw into EDTA-containing microfuge tubes and chilled on ice. Liver samples are collected by necropsy and are flash-frozen in liquid nitrogen and stored at −80 degrees Celsius. For RNA isolation from liver, five to ten mg of frozen liver is placed in 700 µl of 1× Nucleic Acid Lysis Solution (Applied Biosystems Inc., Foster City, Calif.) and homogenized using a hand-held tissue macerator (Biospec Products Inc., Bartlesville, Okla.). The homogenate is filtered through an ABI Tissue pre-filter (Applied Biosystems Inc., Foster City, Calif.) and collected in a deep well plate on an ABI 6100 Nucleic Acid prep station (Applied Biosystems Inc., Foster City, Calif.). The filtered homogenate is then loaded onto an RNA isolation plate and the RNA Tissue-Filter-DNA method is run on the ABI 6100. The isolated RNA is eluted in 150 µl of RNase free water. For quality assessment, 9 µl of the isolated RNA solution is loaded onto a 1% TBE agarose gel, and the RNA is visualized by ethidium bromide fluorescence.

Complementary DNA (cDNA) is synthesized using the ABI High Capacity Archive Kit (Applied Biosystems Inc., Foster City, Calif.). Briefly, a 2× reverse transcriptase Master Mix is prepared according to the manufacturer's protocol for the appropriate number of samples (RT Buffer, dNTP, Random Primers, MultiScribe RT (50 U/µl), RNase free water). For each reaction, 50 µl of 2× RT Master Mix is added to 50 µl of isolated RNA in a PCR tube that is incubated in a thermocycler (25° C. for 10 minutes followed by 37° C. for 2 hours). The resultant cDNA preparation is diluted 1:100 in dH2O for analysis by real-time PCR. Also, a standard curve of cDNA is diluted 1:20, 1:100, 1:400, 1:2000, 1:10,000 for use in final quantitation.

A real-time PCR Master Mix for mouse Cyp4A1 gene expression is mixed to contain:
- 1× Taqman Universal PCR Master Mix (Applied Biosystems Inc., Foster City, Calif.)
- 6 micromolar final concentration Forward primer; Qiagen/Operon Technologies, Alameda, Calif.)
- 6 micromolar final concentration Reverse primer (Qiagen/Operon Technologies, Alameda, Calif.)
- 0.15 micromolar final concentration Probe (5' 6-FAM and 3' Tamra-Q; Qiagen/Operon Technologies, Alameda, Calif.)
- RNase free water to 10 microliters A real-time PCR Master Mix for the 18S ribosomal RNA control gene expression is mixed to contain
- 1× Taqman Universal PCR Master Mix (Applied Biosystems Inc., Foster City, Calif.)
- 0.34 micromolar Probe/Primer TaqMan® Ribosomal RNA Control Reagents #4308329 Applied Biosystems Inc., Foster City, Calif.)
- RNase free water to 10 microliters For the real-time PCR analysis, 6 ul of the respective Master Mix solution (either Cyp4A1 or 18S) and 4 ul either of diluted cDNA or of Standard Curve samples is added to individual wells of a 384-well plate (n=2 for Standards; n=4 for unknowns). Reactions are performed using the ABI 7900 HT standard universal RT-PCR cycling protocol. Data are analyzed using SDS 2.1 (Applied Biosystems Inc., Foster City, Calif.). Average quantity and standard deviation are calculated automatically for each individual sample, according to the standard curve values. Using Microsoft Excel 2000, mean values for each group of five individual mice is calculated. The mean value of each compound-treated group is divided by the mean value of the vehicle-treated group. The fold induction over the vehicle group is determined by assigning the vehicle group to the value of 1.0, and the fold change of the mean value for each group is expressed as fold-induction versus vehicle (1.0). Data are plotted using Jandel SigmaPlot 8.0.

Monkey Studies

Efficacy Studies

Compounds of the invention may be examined in a dyslipidemic rhesus monkey model. After an oral dose-escalation study for 28 days in obese, non-diabetic rhesus monkeys a determination of HDL-c elevation is made with each dose and compared with pretreatment levels. LDL cholesterol is also determined with each dose. C-reactive protein levels are measured and compared to pretreatment levels.

Compound of Formula 1 may be shown to elevate plasma HDL-cholesterol levels in an African Green Monkey model in a manner similar to that described above in rhesus monkeys.

Two groups of monkeys are placed in a dose-escalating study that consists of one week of baseline measurements, 9 weeks of treatments (vehicle, Compound of Formula I), and four weeks of washout. During baseline, monkeys in all three groups are administered vehicle once daily for seven days. Test compound of Formula I, is administered in vehicle once daily for three weeks, then at a greater concentration (double the dose may be desired) once daily for three weeks, and then a still greater concentration (double the most recent dose may be desired) once daily for three weeks. At the completion of treatment, monkeys in both groups are administered vehicle once daily and monitored for an additional six weeks.

Animals are fasted overnight and then sedated for body weight measurements and blood collection at weeks 1 (vehicle), 2, 3, 4, 6, 7, 9, 10, 12, and 14 of the study.

Parameters to measured, for example:
Body weight
Total plasma cholesterol
HDL
LDL
Triglycerides
Insulin
Glucose
PK parameters at week 4, 7, and 10 (plasma drug concentration at last week of each dose)
ApoAI
ApoAII
ApoB
ApoCIII
Liver enzymes (SGPT, SGOT, □GT)
Complete blood count Additionally, other measures may be made, as appropriate, and consistent with the stated study design.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound of the Formula I:

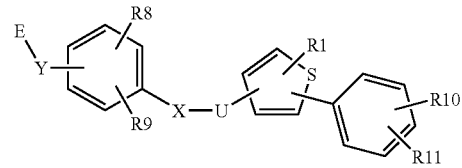

or stereoisomers or pharmaceutically acceptable salts thereof, wherein:
(a) R1 is selected from the group consisting of hydrogen, $C_1$-$C_8$ alkyl, $C_1$-$C_8$ alkenyl, phenyl, and C3-C6 cycloalkylaryl-$C_{0-2}$-alkyl, wherein $C_1$-$C_8$ alkyl is optionally substituted with from one to three substituents independently selected from R1'; and further wherein $C_1$-$C_8$ alkenyl, phenyl, , and C3-C6 cycloalkylaryl-$C_{0-2}$-alkyl, are each optionally substituted with from one to three substituents independently selected from R2;
(b) R1' are each independently selected from the group consisting of hydroxy, cyano, nitro, halo, oxo, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{1-4}$-alkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;
(c) R2, R26, R27, R28, and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$;

(d) X is O;

(e) U is an aliphatic linker;

(f) Y is selected from the group consisting of C, O, S, NH and a single bond;

(g) E is C(R3)(R4)A wherein
   (i) A is selected from the group consisting of carboxyl, , $C_1$-$C_6$ alkylnitrile, carboxamide, sulfonamide and acylsulfonamide; wherein sulfonamide, and acylsulfonamide are each optionally substituted with from one to two groups independently selected from R$^7$;
   (ii) each R$^7$ is independently selected from the group consisting of hydrogen, $C_1$-$C_6$ haloalkyl, aryl $C_0$-$C_4$ alkyl and $C_1$-$C_6$ alkyl;
   (iii) R3 is selected from the group consisting of hydrogen, $C_1$-$C_5$ alkyl, and $C_1$-$C_5$ alkoxy; and
   (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, cycloalkyl and aryl-alkyl are each optionally substituted with one to three each independently selected from R26; with the proviso that when R1 is $C_1$-$C_8$ alkyl, Y is in a para substituted position with relation to X, and X is selected from the group consisting of a bond and O, then R4 is selected from the group consisting of $C_1$-$C_5$ alkoxy, aryloxy, and aryl$C_0$-$C_4$ alkyl;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl, , $C_1$-$C_6$ allyl, and OR29, and wherein aryl-$C_0$-$C_4$ alkyl are each optionally substituted with from one to three independently selected from R27; R29 is selected from the group consisting of hydrogen and $C_1$-$C_4$ alkyl;

(j) R10 is selected from the group consisting of $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and aryloxy, provided that when the aliphatic linker, U, is $C_1$-$C_3$ alkyl substituted with aryl$C_1$-$C_4$alkyl, then R10 is selected from the group consisting of hydrogen, hydroxy, cyano, nitro, halo, oxo, $C_1$-$C_6$ alkyl, $C_1$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28

(k) R11 is selected from the group consisting of hydrogen, hydroxy, cyano, nitro, halo, oxo, $C_1$-$C_6$ alkyl, $C_1$-$C_6$ alkyl-COOR12", $C_1$-$C_6$ alkoxy, $C_1$-$C_6$ haloalkyl, $C_1$-$C_6$ haloalkyloxy, $C_3$-$C_7$ cycloalkyl, aryl-$C_{0-4}$-alkyl, aryl-$C_{1-4}$heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three independently selected from R28; and (l) R12', R12", R13', R14', R15', R16', R17', R18', R19', R20', R21', R22', R23', R24', and R25' are each independently selected from the group consisting of hydrogen, $C_1$-$C_6$ alkyl and aryl; or the compound of Formula I is 3-{2-Methyl-4-[5-(4-trifluoromethyl-phenyl)-thiophen-2-ylmethoxy]-phenyl}-propionic acid.

2. A compound as claimed by claim 1 wherein R4 is selected from the group consisting of $C_1$-$C_5$ alkoxy, aryloxy, and aryl$C_0$-$C_4$ alkyl.

3. A compound as claimed by claim 1 wherein Y is O.

4. A compound as claimed by claim 2 wherein Y is C.

5. A compound as claimed by claim 2 wherein Y is S.

6. A compound as claimed by claim 1 wherein A is carboxyl.

7. A compound as claimed by claim 1 wherein R1 is H.

8. A compound as claimed by claim 7 wherein A is COOH and R1 is H.

9. A compound as claimed by claim 8 wherein R10 is haloalkyl.

10. A compound as claimed by claim 1 wherein R10 is $CF_3$.

11. A compound as claimed by claim 8, wherein R10 is haloalkyloxy.

12. A compound as claimed by claim 1 wherein R10 and R11 are each independently selected from the group consisting of hydrogen, halo, oxo, $C_1$-$C_6$ alkyl, $C_1$-$C_6$ alkyl-COOR12", $C_1$-$C_6$ alkoxy, $C_1$-$C_6$ haloalkyl, and $C_1$-$C_6$ haloalkyloxy.

13. A compound as claimed by claim 1 wherein R10 is selected from the group consisting of $C_3$-$C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and aryloxy.

14. A compound as claimed by claim 1 wherein R8 and R9 are each independently selected from the group consisting of hydrogen and $C_1$-$C_3$ alkyl.

15. A compound as claimed by claim 1 wherein R3 and R4 are each independently selected from the group consisting of $C_1$-$C_2$ alkyl.

16. A compound as claimed by claim 1 wherein R3 and R4 are each independently selected from the group consisting of hydrogen and $C_1$-$C_2$ alkyl.

17. A compound as claimed by claim 1 wherein U is $C_1$-$C_3$ alkyl.

18. A compound as claimed by claim 17 wherein U is saturated.

19. A compound as claimed by claim 17, wherein U is substituted with $C_1$-$C_3$ alkyl.

20. A compound as claimed by claim 17, wherein U is substituted with aryl$C_1$-$C_4$alkyl.

21. A compound as claimed by claim 1 wherein R1 is phenyl.

22. A compound as claimed by claim 1 represented by the following Structural Formula II:

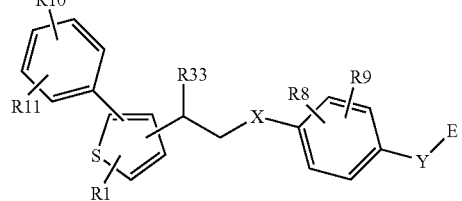

wherein R33 is aryl$C_1$-$C_4$ alkyl.

23. A compound as claimed by claim 1 represented by the following Structural Formula III:

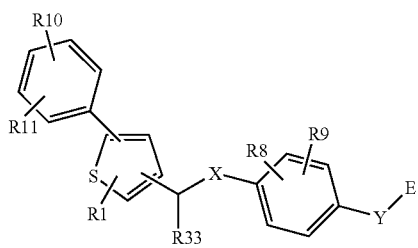

R33 is selected from the group consisting of hydrogen, $C_1$-$C_3$ alkyl, and aryl$C_0$-$C_4$ alkyl.

24. A compound as claimed by claim 1 represented by the following Structural Formula IV:

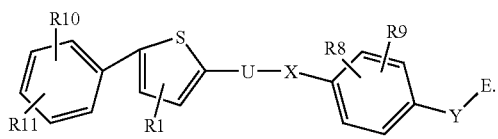

25. A compound as claimed by claim 1 wherein the headpiece of Formula I is:

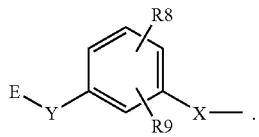

26. A compound as claimed by claim 1, wherein the compound is selected from the group consisting of(2-Methyl-4-{2-[3-methyl-5-(4-trifluoromethyl-phenyl)-thiophen-2-yl]-propylsulfanyl}-phenoxy)-acetic acid, (2-Methyl-4-{2-[3-methyl-5-(4-trifluoromethyl-phenyl)-thiophen-2-yl]-propylsulfanyl}-phenoxy)-acetic acid, and 3-(2-Methyl-4-{2-[3-methyl-5-(4-trifluoromethyl-phenyl)-thiophen-2-yl]-propylsulfanyl}-phenyl)-propionic acid.

27. A compound as claimed by claim 1 that is (3-{2-[3-Methyl-5-(4-trifluoromethyl-phenyl)-thiophen-2-yl]-propoxy}-phenyl)-acetic acid.

28. A compound as claimed by claim 1 wherein the compound is selected from the group consisting of

| Compound | Name |
|---|---|
| ![structure] | 3-{2-Methyl-4-[5-(4-trifluoromethyl-phenyl)-thiophen-2-ylmethoxy]-phenyl}-propionic acid |
| ![structure] | 3-{2-Methyl-4-[3-phenyl-5-(4-trifluoromethyl-phenyl)-thiophen-2-ylmethoxy]-phenyl}-propionic acid |
| ![structure] | 3-{4-[3,5-Bis-(4-trifluoromethyl-phenyl)-thiophen-2-ylmethoxy]-2-methyl-phenyl}-propionic acid. |

29. A compound as claimed by claim 1 which is 3-{2-Methyl-4-[5-(4-trifluoromethyl-phenyl)-thiophen-2-yl-methoxy]-phenyl}-propionic acid.

30. A compound as claimed by claim 1 which is the S conformation.

31. A compound as claimed by claim 1 which is the R conformation.

32. A pharmaceutical composition, comprising as an active ingredient, at least one compound as claimed by claim 1 together with a pharmaceutically acceptable carrier or diluent.

33. A method of mitigating the progression of the symptoms associated with diabetes mellitus in a mammal, comprising the step of administering to the mammal in need thereof, a therapeutically effective amount of at least one compound of claim 1.

34. A method of mitigating the progression of the symptoms associated with atherosclerosis in a mammal, comprising the step of administering to the mammal in need thereof a therapeutically effective amount of at least one compound of claim 1.

35. A compound as claimed by claim 1 for use as a pharmaceutical.

36. A compound as claimed by claim 1 wherein the compound is radiolabeled.

\* \* \* \* \*